(12) United States Patent
Jacobson et al.

(10) Patent No.: US 11,304,963 B2
(45) Date of Patent: Apr. 19, 2022

(54) METHODS OF MEDICAL TREATMENT WITH SUR1-TRPM4 CHANNEL INHIBITORS

(71) Applicant: BIOGEN CHESAPEAKE LLC, Cambridge, MA (US)

(72) Inventors: Sven Jacobson, New York, NY (US); Thomas Macallister, New York, NY (US)

(73) Assignee: Biogen Chesapeake LLC, Cambridge, MA (US)

( * ) Notice: Subject to any disclaimer, the term of this patent is extended or adjusted under 35 U.S.C. 154(b) by 330 days.

(21) Appl. No.: 16/321,149

(22) PCT Filed: Jul. 28, 2017

(86) PCT No.: PCT/US2017/044442
§ 371 (c)(1),
(2) Date: Jan. 28, 2019

(87) PCT Pub. No.: WO2018/023035
PCT Pub. Date: Feb. 1, 2018

(65) Prior Publication Data
US 2019/0175624 A1    Jun. 13, 2019

Related U.S. Application Data

(60) Provisional application No. 62/368,386, filed on Jul. 29, 2016, provisional application No. 62/368,411, filed on Jul. 29, 2016, provisional application No. 62/368,422, filed on Jul. 29, 2016, provisional application No. 62/368,436, filed on Jul. 29, 2016.

(51) Int. Cl.
| | |
|---|---|
| *A61K 31/64* | (2006.01) |
| *A61P 25/00* | (2006.01) |
| *A61K 45/06* | (2006.01) |
| *A61K 31/7076* | (2006.01) |
| *A61K 38/49* | (2006.01) |
| *A61P 25/06* | (2006.01) |
| *A61K 9/00* | (2006.01) |
| *A61K 9/70* | (2006.01) |
| *A61K 31/4045* | (2006.01) |
| *A61K 38/48* | (2006.01) |
| *A61N 5/10* | (2006.01) |

(52) U.S. Cl.
CPC ............ *A61K 31/64* (2013.01); *A61K 9/0053* (2013.01); *A61K 9/7023* (2013.01); *A61K 31/4045* (2013.01); *A61K 31/7076* (2013.01); *A61K 38/482* (2013.01); *A61K 38/4893* (2013.01); *A61K 38/49* (2013.01); *A61K 45/06* (2013.01); *A61N 5/1084* (2013.01); *A61P 25/00* (2018.01); *A61P 25/06* (2018.01); *C12Y 304/21068* (2013.01); *C12Y 304/21069* (2013.01); *C12Y 304/24069* (2013.01)

(58) Field of Classification Search
CPC combination set(s) only.
See application file for complete search history.

(56) References Cited

U.S. PATENT DOCUMENTS

| | | |
|---|---|---|
| 2005/0089473 A1 | 4/2005 | Black et al. |
| 2009/0137680 A1* | 5/2009 | Simard ................ A61K 31/365 514/592 |
| 2010/0092469 A1 | 4/2010 | Simard et al. |
| 2014/0080811 A1 | 3/2014 | Jacobson et al. |

OTHER PUBLICATIONS

Allen, L et al., eds. Ansels Pharm Dosage Forms & Drug Deliv Syst. Lippicott 2005 excerpt.*
Pallan, T. et al., J. Vascular and Interventional Neurology 2014 vol. 7, pp. 22-24.*
Extended Search Report cited in EP17835364.5 dated Jun. 24, 2020, 15 pages.
Communication pursuant to Rule 164(1) EPC cited in EP application No. 17835364.5 dated Mar. 3, 2020, 16 pages.
Notification of Transmittal of the International Search Report and The Written Opinion cited in PCT/US2017/44442, dated Oct. 12, 2017, 14 pages.
Notice of Reasons for Rejections issued in Japanese Application No. 2019-504840, dated Jun. 21, 2021, 5 pages.

* cited by examiner

*Primary Examiner* — Heidi Reese
(74) *Attorney, Agent, or Firm* — Rothwell, Figg, Ernst & Manbeck, P.C.

(57) ABSTRACT

A method of treating or preventing adverse outcomes associated with tissue plasminogen activator (tPA) administration, cerebral edema-related side effects, cerebral edema associated with radiation therapy, or migraine headaches by administering an effective amount of a SUR1-TRPM4 channel inhibitor, such as glyburide, and optionally the co-administration of a second therapeutically active agent, to a subject in need thereof. Adverse outcomes associated with tPA include cerebral hemorrhage, cerebral edema, physical impairment or death. The administration of the SUR1-TRPM4 channel inhibitors occurs prior to the radiation therapy, during the radiation therapy, after the radiation therapy, or combinations thereof. The SUR1-TRPM4 channel inhibitor is administered prior to surgical excision of a brain tumor, CAR-T therapy, or administration of flutarabine. Alternatively, or in addition, the SUR1-TRPM4 channel inhibitor is administered prior the onset of the cerebral edema-related side effects.

11 Claims, 3 Drawing Sheets

FIG. 1 Mean Plasma Glyburide Concentration-Time Profile at Two Dosage Levels
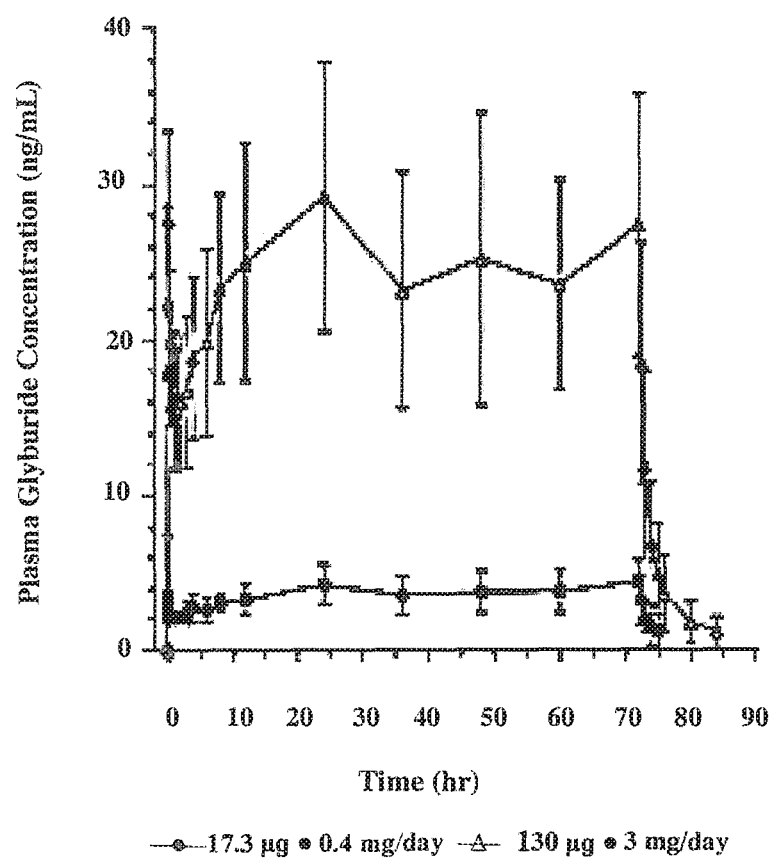

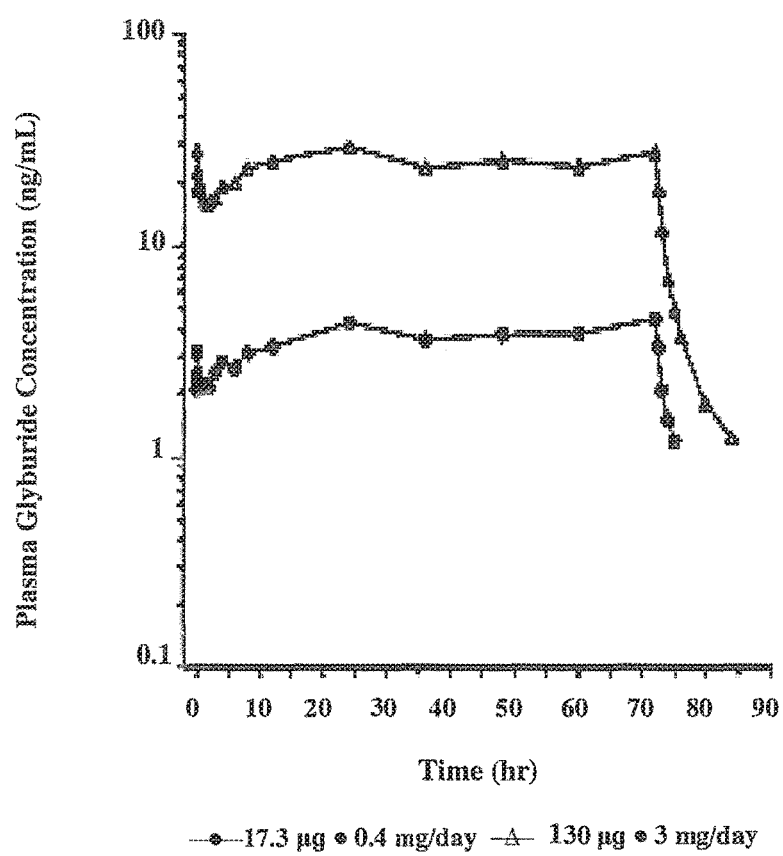
FIG. 2 Mean Plasma Glyburide Concentration-Time Profile at Two Dosage Levels on a Semi-Logarithmic Scale

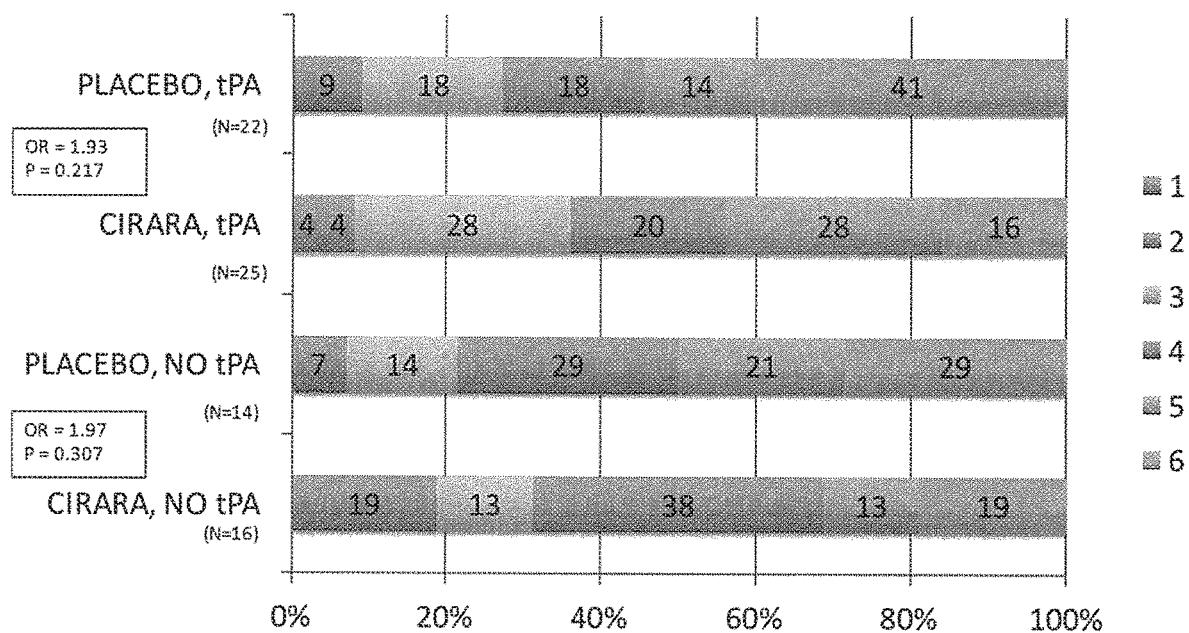
FIG.3 Improved Outcome of tPA with Administration of Cirara

METHODS OF MEDICAL TREATMENT WITH SUR1-TRPM4 CHANNEL INHIBITORS

CROSS-REFERENCE TO RELATED APPLICATIONS

This application is a 35 U.S.C. 371 National Phase Entry Application from PCT/US2017/044442, filed Jul. 28, 2017, which claims the benefit under 35 U.S.C. § 119(e) of the filing date of provisional patent application Ser. No. 62/368,386, filed Jul. 29, 2016, provisional patent application Ser. No. 62/368,411, filed Jul. 29, 2016, provisional patent application Ser. No. 62/368,422, filed Jul. 29, 2016, provisional patent application Ser. No. 62/368,436, filed Jul. 29, 2016, the disclosures of which are incorporated herein by reference in their entirety.

FIELD OF THE INVENTION

This invention relates to the field of medical treatment methods, including intravenous methods of administration of drugs to a subject.

BACKGROUND

There is a need in the field for new methods of treating or preventing one or more adverse outcomes associated with tissue plasminogen activator (tPA) administration.

There is a need in the field for new methods of treating or preventing cerebral edema associated with radiation therapy.

There is a need in the field for new methods of treating or preventing migraine headaches.

There is a need in the field for new methods of treating or preventing one or more cerebral edema-related side effects associated with treatment of a patient.

SUMMARY OF THE INVENTION

The present disclosure is drawn to methods of treating or preventing one or more adverse outcomes associated with tissue plasminogen activator (tPA) such as cerebral hemorrhage, cerebral edema, physical impairment, death, or related outcomes. The methods include treating or preventing adverse outcomes when tPA is administered within the established therapeutic window of 4.5 hours of stroke onset, and administration of at least one SUR1-TRPM4 channel inhibitor.

In several embodiments, administration of an effective amount of a SUR1-TRPM4 channel inhibitor, such as glyburide, in a subject in need of tPA administration occurs prior to the administration of tPA. In several other embodiments, the administration of a SUR1-TRPM4 channel inhibitor occurs during the administration of tPA. In several other embodiments, the administration of a SUR1-TRPM4 channel inhibitor occurs following the administration of tPA. In further embodiments, the administration of a SUR1-TRPM4 channel inhibitor may occur at any time prior to, during, or following the administration of tPA or any combination thereof.

The present disclosure is drawn to methods of treating or preventing one or more cerebral edema-related side effects associated with treatment of a patient. The methods include administering an effective amount of SUR1-TRPM4 channel inhibitor into a patient exhibiting or at risk of cerebral edema-related side effects.

In several embodiments, administration of an effective amount of a SUR1-TRPM4 channel inhibitor, such as glyburide, in a subject in need of or receiving a treatment that is prone to cerebral edema-related side effects occurs prior to the initiation of the treatment. In several other embodiments, the administration of a SUR1-TRPM4 channel inhibitor occurs after the initiation of the treatment that is prone to cerebral edema-related side effects. In other embodiments, the SUR1-TRPM4 channel inhibitor is administered prior to or after the onset of the cerebral edema-related side effects. In further embodiments, the administration of a SUR1-TRPM4 channel inhibitor may occur at any time prior to, during, or following the initiation of the treatment or the onset of the cerebral edema-related side effects.

The present disclosure is drawn to methods of treating or preventing migraine headaches in patients in need of treatment. The methods relate to administration of at least one SUR1-TRPM4 channel inhibitor in the subject in an amount effective to reduce the symptoms of migraine headaches.

In several embodiments, an effective amount of a SUR1-TRPM4 channel inhibitor, such as glyburide, is administered prior to the onset of the migraine. In several other embodiments, the administration of a SUR1-TRPM4 channel inhibitor occurs after the onset of the migraine. In further embodiments, the administration of a SUR1-TRPM4 channel inhibitor may occur at any time prior to, during, or following the onset of the migraine or any combination thereof. In embodiments, a second therapeutically active agent is co-administered with the SUR1-TRPM4 channel inhibitor. In any embodiment, the administration may last for about 1 hours to about 96 hours or longer.

The present disclosure is drawn to methods of treating or preventing cerebral edema in subjects undergoing radiation therapy. The methods include administration of an effective amount of SUR1-TRPM4 channel inhibitor to a patient who is receiving or may receive radiation therapy in or around the brain.

In several embodiments, administration of an effective amount of a SUR1-TRPM4 channel inhibitor, such as glyburide, in a subject in need of or receiving radiation therapy occurs prior to the initiation of the therapy. In several other embodiments, the administration of a SUR1-TRPM4 channel inhibitor occurs during the radiation therapy. In several other embodiments, the administration of a SUR1-TRPM4 channel inhibitor occurs after the initiation of the radiation therapy. In other embodiments, the SUR1-TRPM4 channel inhibitor is administered prior to or after the onset of the cerebral edema associated with radiation therapy. In further embodiments, the administration of a SUR1-TRPM4 channel inhibitor may occur at any time prior to, during, or following the initiation of the radiation therapy or the onset of the cerebral edema.

BRIEF DESCRIPTION OF THE FIGURES

References will now be made to exemplary embodiments illustrated, and specific language will be used herein to describe the same. It will nevertheless be understood that these drawings merely depict exemplary embodiments and are not, therefore, to be considered limiting of its scope.

FIG. 1 shows the mean plasma glyburide concentration time profiles following a bolus injection and 72 hours of intravenous infusion of glyburide at two dosage levels. The data is shown on a linear scale with Plasma Glyburide Concentration in ng/mL on the vertical axis and Time in hours on the horizontal axis.

FIG. 2 shows the mean plasma glyburide concentration time profiles from the same study depicted in FIG. 1. The data is presented on a semi-logarithmic scale with Plasma Glyburide Concentration in ng/mL on the vertical logarithmic axis and Time in hours on the horizontal axis.

FIG. 3 shows a bar graph comparing the outcome of four study groups. Each group was administered a glyburide containing drug (Cirara), a placebo, tPA, or a combination any of the two. tPA was administered within 4.5 hours of stroke onset, in accordance with current clinical practice guidelines.

DETAILED DESCRIPTION

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof. It is further to be understood that the embodiments disclosed in the following subsections may be combined with other embodiments from the same or other subsections without limit.

SUR1-TRPM4 Channel Inhibitors

A SUR1-TRPM4 channel, also known as a $NC_{CA\text{-}ATP}$ channel, is an ion channel found in the cell membranes of neurons, astrocytes, and other cells in mammals. The ion channel helps maintain the ion gradient between cells and the extracellular fluid and is associated with ion flow and concomitant fluid flow between the intercellular and extracellular space. The ion channel is comprised of subparts including a sulfonylurea receptor 1 (SUR1) and a transient receptor potential cation channel subfamily M member 4 (TRPM4).

A SUR1-TRPM4 channel inhibitor is a compound that selectively binds to the SUR1 and/or the TRPM4 subparts of the SUR1-TRPM4 channel. When the SUR1-TRPM4 channel inhibitor is bound with either part of the ion channel, the ion channel is effectively blocked or "shut-off", resulting in fewer or no ions entering or leaving the cell through that ion channel. The fluid flow into or out of the cell is reduced or stopped due to the stabilization of the ion gradient.

SUR1-TRPM4 channel inhibitors include glyburide, 4-trans-hydroxy-glibenclamide, 3-cis-hydroxyglibenclamide, tobutamide, chlorpropamide, tolazamide, repaglinide, nateglinide, meglitinide, midaglizole, tolazamide, gliquidone, LY397364, LY389382, glyclazide, glimepiride, 9-phenantrol, fluflenamic acid, riluzole, spermine, adenosine, quinine, quinidine, diphenylamine-2-carboxylic acid, 3',5'-dichlorodiphenylamine-2-carboxylic acid, 5-nitro-2-(3-phenylpropyl-amino)-benzoic acid, 5-butyl-7-chloro-6-hydroxybenzo[c]-quinolizinium chloride (MPB-104), metabolites that interact with SUR1, or combinations thereof. As used herein, any reference to a SUR1-TRPM4 channel inhibitor or "channel inhibitor" is understood to be a reference to one or more of the compounds in the preceding list. Additionally, as used herein, glyburide is commonly referred to as a model SUR1-TRPM4 channel inhibitor. The reference to glyburide in specific embodiments or examples is not intended to limit the scope of the invention and is exemplary of all SUR1-TRPM4 channel inhibitors.

Preparation of SUR1-TRPM4 Channel Inhibitor

The SUR1-TRPM4 channel inhibitors may be administered in the form of a bulk active chemical or, preferably, as a pharmaceutical composition or formulation for efficient and effective administration. Depending on the administration route and the desired dosage level, the preparation of the SUR1-TRPM4 channel inhibitor can vary for each embodiment.

For example, the SUR1-TRPM4 channel inhibitor may be prepared in lyophilized form as taught by U.S. Pat. No. 8,858,997, which is hereby incorporated by reference in its entirety. The channel inhibitor may also be prepared as a powdered composition, for example, as disclosed in U.S. Pat. No. 8,277,845, which is hereby incorporated by reference in its entirety.

In some embodiments, the channel inhibitor is prepared in a substantially liquid form suitable for intravenous injection or infusion. For example, a SUR1-TRPM4 channel inhibitor may be included in intravenous fluids containing sugars, amino acids, electrolytes, or other simple chemicals suitable for injection, which are suspended in water, Ringer's solution, U.S.P. or isotonic sodium chloride as taught by U.S. patent application Ser. No. 13/779,511, which is hereby incorporated by reference in its entirety. In such embodiments, the channel inhibitor may be suspended with or without a pharmaceutically acceptable carrier.

For oral administration, the SUR1-TRPM4 channel inhibitor may be prepared as a liquid or solid. For example, liquid forms for oral administration may include pharmaceutically acceptable emulsions, microemulsions, solutions, suspensions, syrups and elixirs as taught by U.S. patent application Ser. No. 13/779,511, which is hereby incorporated by reference in its entirety. Additionally, solid forms for oral administration may be prepared as tablets, capsules, gel capsules, or other know oral delivery systems.

In some embodiments, the channel inhibitor may be prepared as a composition containing at least one other therapeutically active or therapeutically inert compound. For example, a composition containing a SUR1-TRPM4 channel inhibitor and a substance effective to maintain blood pressure and blood glucose levels within an acceptable range may be formulated as taught by U.S. patent application Ser. No. 13/779,511, which is hereby incorporated by reference in its entirety.

In some embodiments, the channel inhibitor may be prepared for co-administration with a second therapeutically active agent. For example, therapeutic agents that treat migraine side effects such as pain relievers, triptan, glucocorticoids, antidepressants, anti-seizure drugs, botox, combinations thereof, or similar drugs may be co-administered with the SUR1-TRPM4 channel inhibitor. The co-administration may occur in the form of a single compound containing both the SUR1-TRPM4 channel inhibitor and the second therapeutically active agent, or as two compounds—one containing SUR1-TRPM4 channel inhibitor and one containing a second therapeutically active agent. In any case, the compounds may be prepared in any form including: liquid, emulsion, powdered, lyophilized, tablets, combinations thereof, and others disclosed herein.

In some embodiments, the ratio of SUR1-TRPM4 channel inhibitor to the second therapeutically active agent is about 75:25. In other embodiments, the ratio of SUR1-TRPM4 channel inhibitor to the second therapeutically active agent is about 25:75. Thus the ratio of SUR1-TRPM4 channel inhibitor to second therapeutically active is contemplated to be about 80:20, or 75:25, or 70:30, or 60:40, or 50:50, or 40:60, or 40:70, or 25:75, or 20:80, or ranges between any of these values. Of course when the SUR1-TRPM4 channel inhibitor is administered alone, the ratio of SUR1-TRPM4 channel inhibitor to the second therapeutically active agent is substantially 100:0.

Tissue Plasminogen Activator

Tissue plasminogen activator (tPA) is a class of strong blood clot dissolving medicines. It has become the "gold standard" in treating stroke and has been shown effective in improving the chance of survival of patients suffering a stroke. See Tissue Plasminogen Activator for Acute Ischemic Stroke, 333 NEW ENG. J. MED. 1581-88 (Dec. 4, 1995), hereby incorporated in its entirety. There are several adverse outcomes associated with administration of tPA. When one has had minimal blood flow to an area of the brain and blood flow is returned, by the administration of tPA, the area of the brain that was blood deprived is at risk of cerebral hemorrhage, or cerebral edema. The return of blood flow may lead to temporary or permanent physical impairment or death.

Administration of a SUR1-TRPM4 channel inhibitor is effective to prevent or treat the adverse outcomes associated with tPA. For any administration route and for any administration duration, the glyburide or other such drug may be administered prior to, simultaneously, or after the administration of the tPA, or a combination thereof. The glyburide administration may also be administered prior to or after the onset of the adverse effects associated with tPA.

Large hemispheric infarction (LHI) is an ischemic stroke affecting the total or sub-total territory of the middle cerebral artery (MCA) with or without involvement of the adjacent vascular territories like the anterior cerebral artery (ACA) or posterior cerebral artery (PCA) territories. Patients with LHI may also suffer from cerebral edema. LHI is frequently complicated by edema that ultimately may lead to transtentorial herniation and death. For example, the swelling that results from LHI can compress capillary beds and compromise arterial inflow to surrounding tissues, causing further ischemic damage and enlargement of the infarct, and frequently results in brain herniation and death.

Current clinical guidelines recommend administering tPA within 4.5 hours of stroke onset. See Jauch et al., Guidelines for the Early Management of Patients With Acute Ischemic Stroke: A Guideline for Healthcare Professionals From the American Heart Association/American Stroke Association, 44 Stroke 870-947 (2013), the entirety of which is hereby incorporated by reference. A longer therapeutic window is confounded by the risk of hemorrhagic transformation. Administration of tPA is used to return blood flow to the affected area in an attempt to abate the infarction; however, the tPA aggravates the edema in LHI as blood flow returns to the area and the brain swells further. Administration of a SUR1-TRPM4 channel inhibitor to patients with LHI prior to the tPA administration and/or during and/or after the tPA administration, may prevent further cerebral edema as blood flow is returned to the area and/or may reduce the cerebral edema present in LHI patients. For example, LHI patients excluded from mechanical thrombectomy due to large lesion size are likely to benefit from edema-reducing pharmacotherapy like a SUR1-TRPM4 channel inhibitor. Consistently, current clinical guidelines recommend exclusion of infarctions involving more than one-third of the middle cerebral artery territory.

Preferably, a SUR1-TRPM4 channel inhibitor (e.g., glyburide) is administered before, during, and/or after tPA administration to a patient lesion volume of 80-300 mls as measured by magnetic resonance imaging diffusion weighted imaging or CT perfusion or those with an Alberta Stroke Program Early CT Score (ASPECTS) that is equal to or less than 7, or equal to or less than 6, or equal to or less than 5, or equal to or less than 4, or equal to or less than 3. ASPECTS measurements are performed according to standard procedures, e.g., Powers et al., American Heart Association/American Stroke Association Focused Update of the 2013 Guidelines for the Early Management of Patients With Acute Ischemic Stroke Regarding Endovascular Treatment: A Guideline for Healthcare Professionals From the American Heart Association/American Stroke Association, Stroke 46(10):3020-3035 (2015); Schröder et al., STIR and VISTA Imaging Investigators, Validity of acute stroke lesion volume estimation by diffusion-weighted imaging-Alberta Stroke Program Early Computed Tomographic Score depends on lesion location in 496 patients with middle cerebral artery stroke, Stroke. 45(12):3583-3588 (2014), the entirety of which are hereby incorporated by reference in their entirety.

The administration of tPA is typically performed by intravenous infusion, but tPA may be administered in any manner including but not limited to infusion, oral, or subcutaneous administration. Examples of tPAs include activase, tenectoplase, eurokinase, streptokinase, and desmoteplase.

SUR1-TRPM4 Administration

The manner and duration of administering SUR1-TRPM4 channel inhibitor may vary. Regardless of administration route, embodiments may be administered for about 5 to about 96 hours or longer. For example, the administration duration may be from about 1-5 hours, from about 5-10 hours, from about 10-15 hours, from about 15-20 hours, from about 20-25 hours, from about 25-30 hours, from about 30-35 hours, from about 35-40 hours, from about 40-45 hours, from about 45-50 hours, from about 50-55 hours, from about 55-60 hours, from about 60-65 hours, from about 65-70 hours, from about 70-75 hours, from about 75-80 hours, from about 80-85 hours, from about 85-90 hours, or from about 90-96 hours. In other embodiments, administration of the SUR1-TRPM4 channel inhibitor extends over periods of more than about 5 hours, or more than about 10 hours, or more than about 20 hours, or more than about 30 hours, or more than about 40 hours, or more than about 50 hours, or more than about 60 hours, or more than about 70 hours, or more than about 80 hours, or more than about 90 hours. In further embodiments, the SUR1-TRPM4 inhibitor administration last from about 5 hours to about 90 hours, from about 15 hours to about 80 hours, from about 25 hours to about 70 hours, from about 35 hours to about 60 hours, or from about 45 to 50 hours.

In other embodiments, the administration may occur for an extended period of time, such as a period of about one day, or about two days, or about three days, or about four days, or about five days, or more. For patients with chronic conditions, the administration may last even longer, such as several days, or about 1 week, or about 2 weeks, or about 3 weeks, or more until symptoms subside.

In further embodiments, the SUR1-TRPM4 administration may occur about 6 hours or less prior to administration of tPA. As such, embodiments may begin administration about 6 hours prior to the administration of tPA, about 5 hours prior to the administration of tPA, about 4 hours prior to the administration of tPA, about 3 hours prior to the administration of tPA, about 2 hours prior to the administration of tPA, or about 1 hour or less prior to the administration of tPA. Such embodiments may administer the SUR1-TRPM4 channel inhibitor intermittently for a duration listed above or continuously for the duration listed above.

For any given administration duration, the administration may occur continuously or as a series of separate administrations, and also may include more than one SUR1-TRPM4 channel inhibitor and/or more than one route of administration.

In some embodiments, the SUR1-TRPM4 channel inhibitor is administered via one or more continuous infusions. A continuous infusion is an intravenous administration that may last for any of the above listed durations. In further embodiments, the administration includes at least two continuous infusions where there is about 1 to several minutes, about 1 to several hours, about 1 to several days, or about 1 to several months between the multiple continuous infusions. The at least two continuous infusions may administer the same or different SUR1-TRPM4 channel inhibitors.

In some embodiments, the SUR1-TRPM4 channel inhibitor administration is achieved by injection. An injection is an intravenous administration that may be continuous or bolus in form. A continuous injection is one that lasts for any duration stated above. A bolus injection refers to administration of the SUR1-TRPM4 channel inhibitor in a single injection that lasts for a relatively short period of time, usually a period of about 3 minutes or less. Several bolus injections may be administered in series for any of the durations disclosed above.

In further embodiments, the methods of administration include administration of the SUR1-TRPM4 channel inhibitor in a bolus injection to a subject, followed by a continuous infusion of the SUR1-TRPM4 channel inhibitor and by one or more further bolus injections of the SUR1-TRPM4 channel inhibitor. In embodiments, a second bolus injection is administered substantially immediately after the completion of the continuous infusion. For example, the second bolus administration commences less than one hour, or less than 30 minutes, or less than 10 minutes, or less than 5 minutes, or less than 3 minutes, or less than 2 minutes, or less than 1 minute, after the completion of the continuous infusion. A third bolus injection may begin after the completion of the second continuous infusion, and may begin either substantially immediately after the completion of the second continuous infusion, or may begin after an extended period of time after the completion of the second continuous infusion. Similarly, a fourth, or fifth, or other further bolus injection, and/or further continuous infusion may be administered, either substantially immediately, or after an extended period of time. It is contemplated that the entire sequence of bolus injections and continuous infusions may occur wholly prior to or after the administration of tPA, or the sequence may be split between before, during, and after the administration of tPA with one or more bolus injections and/or one or more continuous infusions occurring before, one or more bolus injections and/or continuous administrations occurring during, and/or one or more bolus injections and/or continuous infusions occurring after the administration of tPA. Intravenous administration methods disclosed in U.S. Pat. No. 9,254,259 may be used, which is hereby incorporated by reference in its entirety.

In other embodiments, the SUR1-TRPM4 channel inhibitor is administered transdermally. An advantage of transdermal administration is that it may be less invasive as compared to administration by infusion or injection and may be more effective than oral pathways. For example, the SUR1-TRPM4 channel inhibitor may be administered using a transdermal patch taught in Manoj K. Mishra, *Microcapsules and Transdermal Patch: A Comparative Approach for Improved Delivery of Antidiabetic Drug*, 10 AAPS PHARM. SCI. TECH. 3, 928-34 (2009), which is hereby incorporated by reference in its entirely. Optionally, the drug may be administered through a transdermal gel as taught in Srinivas Mutalik & Nayanabhirama Udupa, *Pharmacological Evaluation of Membrane-Moderated Transdermal Systems of Glipizide*, 33 CLINICAL & EXPERIMENTAL PHARMACOLOGY & PHYSIOLOGY, 17-26 (2006), which is hereby incorporated by reference in its entirety. For example, transdermal administration may be used for subjects with chronic conditions who may benefit from continuous and/or prolonged administration of SUR1-TRPM4 channel inhibitors. The transdermal administration may occur for any duration disclosed above. Administration through a transdermal patch or gel may occur prior to, simultaneously with, and/or after the administration of tPA, or any combination thereof. In further embodiments, the transdermal administration may accompany an oral, injection, or infusion administration disclosed above or combinations thereof.

In further embodiments, the SUR1-TRPM4 channel inhibitor is administered orally. The oral administration may be via capsules, tablets, pills, powders, liquid suspension, or other commonly used oral administration forms. The oral administration may occur prior to, during, or after the administration of tPA, or any combination thereof. In further embodiments, the oral administration may be combined with an injection, infusion, or transdermal administration route disclosed herein or combinations thereof.

In all embodiments, the administration of the SUR1-TRPM4 channel inhibitor can be intermittent, or at gradual, continuous, constant, or controlled rates. In addition, the time of day and the number of times per hour, day, week, or month that the compounds are administered can vary depending upon desired dosages.

Dosage Determinations

As used herein, the term "dose" and its grammatical derivatives and equivalents refers to the amount of SUR1-TRPM4 channel inhibitor administered to a subject. A dose may be described in terms of weight of a SUR1-TRPM4 channel inhibitor administered per day, in terms of the weight of SUR1-TRPM4 channel inhibitor per volume, or in equivalent types of measurements. The term "effective amount" or "effective dose" refers to the amount of a compound (e.g., a compound of the present invention) sufficient to effect beneficial or desired results. An effective amount can be administered in one or more administrations, applications or dosages and is not intended to be limited to a particular formulation or administration route.

It is understood that an effective amount of a SUR1-TRPM4 channel inhibitor as a treatment may vary depending on several factors including the specific subject receiving the administration, the administration route, the likelihood or severity of adverse outcomes, the duration or amount of tPA administration, and other procedure specific conditions. It will also be understood that dosages will vary between different SUR1-TRPM4 channel antagonists.

In one embodiment of the invention, the effective dosage level is measured in mg of SUR1-TRPM4 channel inhibitor per day and ranges from about 0.05 mg/day to about 3.0 mg/day. For example, a suitable daily dose of SUR1-TRPM4 channel inhibitor may be less than about 3.0 mg per day. For example, a suitable daily dose of glyburide may be about 2.5-3.0 mg/day, or about 2.0-2.5 mg/day, or about 1.5-2.0 mg/day, or about 1.0-1.5 mg/day, or about 0.4-1.0 mg/day, or about 0.05-0.4 mg/day. Additionally, the suitable daily dose may be about 0.05 mg/day, or about 0.25 mg/day, or about 0.5 mg/day, or about 1.0 mg/day, or about 1.5 mg/day, or about 2.0 mg/day, or about 2.5 mg/day, or about 3.0 mg/day. The effective dose for a given patient may also range from about 0.05 mg/day to about 3.0 mg/day, or from about 0.5 mg/day to about 2.5 mg/day, or from about 1.0 mg/day to about 2.0 mg/day. The SUR1-TRPM4 dosage levels are calculated in mg/day for illustrative purposes but the listed ranges are intended to include analogous dosages calculated in any weight unit per hour, day, week, month, treatment session, or similar time period.

Optionally, the dose range of the SUR1-TRPM4 channel inhibitor is an amount that yields a SUR1-TRPM4 blood plasma level of about 0.4 ng/mL to about 5 ng/mL. Suitable blood plasma concentrations include about 5 ng/mL, or about 4.5 ng/mL, or about 4 ng/mL, or about 3.5 ng/mL, or about 3 ng/mL, or about 2.5 ng/mL, or about 2 ng/mL or about 1.5 ng/mL, or about 1 ng/mL, or about 0.5 ng/mL, or similar blood plasma concentrations. In some embodiments, the suitable blood plasma concentration of the SUR1-TRPM4 inhibitor may be about 0.4-1.0 ng/mL, or about 1.0-1.5 ng/mL, or about 1.5-2.0 ng/mL, or about 2.0-2.5 ng/mL, or about 2.5-3.0 ng/mL, or about 3.0-3.5 ng/mL, or about 3.5-4.0 ng/mL, or about 4.0-4.5 ng/mL, or about 4.5-5.0 ng/mL, or combinations thereof. A suitable plasma concentration may also fall in the range of about 0.5 ng/mL to about 5.0 ng/mL, or of about 1.0 ng/mL to about 4.5 ng/mL, or of about 1.5 ng/mL to about 4.0 ng/mL, or of about 2.0 ng/mL to about 3.5 ng/mL, or of about 2.5 ng/mL to about 3.0 ng/mL. The amounts listed are intended for illustrative purposes and it is understood that any dosage levels substantially similar to those listed are covered by the present invention. The ranges are also intended to encompass analogous ranges measured in any units of weight of drug per any unit of blood plasma volume.

Optionally, the effective dose level is one that reaches a maximum SUR1-TRPM4 channel inhibitor plasma concentration level (denoted as "$C_{max}$") of about 1 ng/mL to about 30 ng/mL. Suitable maximum SUR1-TRPM4 channel concentrations include about 30 ng/mL, about 28 ng/mL, about 26 ng/mL, about 24 ng/ML, about 22 ng/mL, about 20 ng/mL, about 18 ng/mL, about 16 ng/mL, about 14 ng/mL, about 12 ng/mL, about 10 ng/mL, about 8 ng/mL, about 6 ng/mL, about 4 ng/mL, about 2 ng/mL, or about 1 ng/mL, or similar concentration levels. A suitable maximum concentration level may also fall in the range of about 1-2 ng/mL, about 2-4 ng/mL, about 4-6 ng/mL, about 6-8 ng/mL, about 8-10 ng/mL, about 10-12 ng/mL, about 12-14 ng/mL, about 14-16 ng/mL, about 16-18 ng/mL, about 18-20 ng/mL, about 20-22 ng/mL, about 22-24 ng/mL, about 24-26 ng/mL, about 26-28 ng/mL, or about 28-30 ng/mL. It is understood that any dosage levels substantially similar to those listed are covered by the present invention. The ranges are intended to encompass analogous ranges measured in any units of weight of drug per any unit of volume.

Optionally, the effective dose level is one that achieves a steady-state SUR1-TRPM4 concentration of about 3.0 ng/mL to about 30.0 ng/mL. Thus, in embodiments, treatment will result in stead-state blood plasma concentrations of about 30 ng/mL, about 27 ng/mL, about 24 ng/mL, about 21 ng/mL, about 18 ng/mL, about 15 ng/mL, about 12 ng/mL, about 9 ng/mL, about 6 ng/mL, about 3 ng/mL, or anywhere between the listed concentrations. In other embodiments, the desired effective steady-state concentration may be about 3.0-5.0 ng/mL, or about 5.0-7.0 ng/mL, or about 7.0-10.0 ng/mL, or about 10.0-12.0 ng/mL, or about 12.0-14.0 ng/mL, or about 14.0-16.0 ng/mL, or about 16.0-18.0 ng/mL, or about 18.0-20.0 ng/mL, or about 20.0-22.0 ng/mL, 22.0-24.0 ng/mL, or about 24.0-26.0 ng/mL, or about 26.0-28.0 ng/mL, or about 28.0-30.0 ng/mL, or combinations thereof. In further embodiments, a steady-state concentration of about 3.0 ng/mL to about 30.0 ng/mL, or about 5.0 ng/mL to about 28.0 ng/mL, or about 7.0 ng/mL to about 26.0 ng/mL, or about 9.0 ng/mL to about 24.0 ng/mL, or about 11.0 ng/mL to about 22.0 ng/mL, or about 13.0 ng/mL to about 20.0 ng/mL, or about 15.0 ng/mL to about 18.0 ng/mL, or about 16.0 ng/mL to about 17.0 ng/mL, or combinations thereof may be desired. The desired steady-state concentration may vary depending on several factors, including the likelihood and/or severity of adverse outcomes, and may change over time. The ranges disclosed are exemplary and are intended to encompass analogous ranges measured in any units of weight per volume.

The specific effective dose for any particular patient will depend on a variety of factors including the severity or likelihood of the condition; activity of the specific compound employed; the age, body weight, general health, sex and diet of the patient; the preparation of the specific compound; the time and route of administration; the duration of administration; therapeutic agents used in combination or coinciding with the specific compound employed; and like factors known in the medical arts. The effective dose may also change over time as any of the adverse outcomes worsen or improve, tracking the progress of adverse outcomes by known methods can help determine dosage levels. For chronic conditions, subjects may receive an effective dose for a plurality of days, weeks, or months. The number of and frequency of administrations may vary depending upon the likelihood or severity of the adverse outcomes and the patient specific response to the particular SUR1-TRPM4 channel inhibitor administered.

For any compound used in the methods described herein, the effective dose may be estimated initially from cell based assays. A dosage may be formulated in animal models to achieve a desired circulating plasma concentration range. Such information can be used to more accurately determine useful doses in humans.

The foregoing description of preferred embodiments has been presented for purposes of illustration and description only. It is not intended to be exhaustive or to limit the application to the precise form disclosed, and modifications and variations are possible and/or would be apparent in light of the above teachings or may be acquired from practice of the application. The embodiments were chosen and described in order to explain the principles of the application and its practical application to enable one skilled in the art to utilize the application in various embodiments and with various modifications as are suited to the particular use contemplated. It is intended that the scope of the application be defined by the claims appended hereto and that the claims encompass all embodiments of the application, including the disclosed embodiments and their equivalents.

Cerebral Edema-Related Side Effects

Cerebral edema is the swelling of neurons and other cells in the brain due to excess fluid in the intracellular space. The swelling may be caused by traumatic brain injury or stroke, as taught by U.S. Pat. No. 8,946,293, hereby incorporated by reference in its entirety, or may be a side effect of medical treatments that disrupt the ion gradients between the intracellular and extracellular space. The latter can be effectively treated or prevented by the administration of a SUR1-TRPM4 channel inhibitor. The channel inhibitor stops or reduces the flow of ions into cells which overtime returns the ion gradient to normal. Fluid flow associated with the ion gradient then also returns to normal and cellular swelling is reduced or eliminated.

There are many medical treatments that may cause cerebral edema. For example, a cancer treatment under development by Juno Therapeutics called chimeric antigen receptor T-cell therapy (CAR-T) is a treatment that administers genetically engineered T-cells and potent chemicals intended to attack cancerous blood cells in patients. See Herper, *Juno Therapeutics Stops Trial of Cancer-Killing Cells After* 3 *Patient Deaths*, FORBES MAG. (Jul. 7, 2016). Following the CAR-T therapy, three patients died unexpectedly from cerebral edema. Administration of SUR1-TRPM4 channel inhibitors before and/or after the CAR-T treatment or before and/or after the onset of cerebral edema-related side effects can treat the cerebral edema and improve the outcome of CAR-T therapy.

Another example of treatments prone to cerebral edema-related side effects is the administration of chemotherapy drugs such as flutarabine. Flutarabine is thought to be the component of the CAR-T therapy that is most likely to cause the cerebral edema. Administration of SUR1-TRPM4 channel inhibitors can counteract the ion gradient disruption caused by the chemicals in flutarabine and similar drugs.

Another example is surgical excision of a brain tumor. Cerebral edema caused by brain tumor excision is a result of the trauma associated with the surgery and the chemicals administered during the procedure and recovery period. Administration of SUR1-TRPM4 prior to and/or after the procedure can reduce the risk of cerebral edema and treat any present cerebral edema.

In some embodiments, the SUR1-TRPM4 channel inhibitor may be administered prior to and/or during and/or after the initiation of the treatment prone to cerebral edema-related side effects. In further embodiments, the SUR1-TRPM4 channel inhibitor may be administered prior to and/or after the onset of the cerebral edema-related side effect The foregoing examples are illustrative and are not intended to limit the scope of the present application. The underlying medical treatment or procedure causing cerebral edema-related side effects can include any treatment or procedure that exhibits such side effects.

SUR1-TRPM4 Administration

The manner and duration of administering SUR1-TRPM4 channel inhibitor may vary. Regardless of administration route, embodiments may be administered for about 1 to about 96 hours or longer. For example, the administration duration may be from about 1-5 hours, from about 5-10 hours, from about 10-15 hours, from about 15-20 hours, from about 20-25 hours, from about 25-30 hours, from about 30-35 hours, from about 35-40 hours, from about 40-45 hours, from about 45-50 hours, from about 50-55 hours, from about 55-60 hours, from about 60-65 hours, from about 65-70 hours, from about 70-75 hours, from about 75-80 hours, from about 80-85 hours, from about 85-90 hours, or from about 90-96 hours. In other embodiments, administration of the SUR1-TRPM4 channel inhibitor extends over periods of more than about 5 hours, or more than about 10 hours, or more than about 20 hours, or more than about 30 hours, or more than about 40 hours, or more than about 50 hours, or more than about 60 hours, or more than about 70 hours, or more than about 80 hours, or more than about 90 hours. In further embodiments, the SUR1-TRPM4 inhibitor administration last from about 5 hours to about 90 hours, from about 15 hours to about 80 hours, from about 25 hours to about 70 hours, from about 35 hours to about 60 hours, or from about 45 to 50 hours.

In other embodiments, the administration may occur for an extended period of time, such as a period of about one day, or about two days, or about three days, or about four days, or about five days, or more. For patients with chronic conditions, the administration may last even longer, such as several days, or about 1 week, or about 2 weeks, or about 3 weeks, or more until symptoms subside.

In further embodiments, the SUR1-TRPM4 administration may occur about 6 hours or less prior to the initiation of the cerebral edema prone treatment. As such, embodiments may begin administration about 6 hours prior to the initiation of the treatment, about 5 hours prior to the initiation of the treatment, about 4 hours prior to the initiation of the treatment, about 3 hours prior to the initiation of the treatment, about 2 hours prior to the initiation of the treatment, or about 1 hour or less prior to the initiation of the treatment. Such embodiments may administer the SUR1-TRPM4 channel inhibitor intermittently for a duration listed above or continuously for the duration listed above.

For any given administration duration, the administration may occur continuously or as a series of separate administrations, and also may include more than one SUR1-TRPM4 channel inhibitor and/or more than one route of administration.

In some embodiments, the SUR1-TRPM4 channel inhibitor is administered via one or more continuous infusions. A continuous infusion is an intravenous administration that may last for any of the above listed durations. In further embodiments, the administration includes at least two continuous infusions where there is about 1 to several minutes, about 1 to several hours, about 1 to several days, or about 1 to several months between the multiple continuous infusions. The at least two continuous infusions may administer the same or different SUR1-TRPM4 channel inhibitors.

In some embodiments, the SUR1-TRPM4 channel inhibitor administration is achieved by injection. An injection is an intravenous administration that may be continuous or bolus in form. A continuous injection is one that lasts for any duration stated above. A bolus injection refers to administration of the SUR1-TRPM4 channel inhibitor in a single injection that lasts for a relatively short period of time, usually a period of about 3 minutes or less. Several bolus injections may be administered in series for any of the durations disclosed above.

In further embodiments, the methods of administration include administration of the SUR1-TRPM4 channel inhibitor in a bolus injection to a subject, followed by a continuous infusion of the SUR1-TRPM4 channel inhibitor and by one or more further bolus injections of the SUR1-TRPM4 channel inhibitor. In embodiments, a second bolus injection is administered substantially immediately after the completion of the continuous infusion. For example, the second bolus administration commences less than one hour, or less than 30 minutes, or less than 10 minutes, or less than 5 minutes, or less than 3 minutes, or less than 2 minutes, or less than 1 minute, after the completion of the continuous infusion. A third bolus injection may begin after the completion of the second continuous infusion, and may begin either substantially immediately after the completion of the second continuous infusion, or may begin after an extended period of time after the completion of the second continuous infusion. Similarly, a fourth, or fifth, or other further bolus injection, and/or further continuous infusion may be administered, either substantially immediately, or after an extended period of time. It is contemplated that the entire sequence of bolus injections and continuous infusions may occur wholly prior to or after the onset of cerebral edema-related side effects, or the sequence may be split between before, during, and after the onset of cerebral edema-related side effects with one or more bolus injections and/or one or more continuous infusions occurring before, one or more bolus injections and/or continuous administrations occurring during, and/or one or more bolus injections and/or continuous infusions occurring after the onset of cerebral edema-related side effects. Intravenous administration methods disclosed in U.S. Pat. No. 9,254,259 may be used, which is hereby incorporated by reference in its entirety.

In other embodiments, the SUR1-TRPM4 channel inhibitor is administered transdermally. An advantage of transdermal administration is that it may be less invasive as compared to administration by infusion or injection and may be more effective than oral pathways. For example, the SUR1-TRPM4 channel inhibitor may be administered using a transdermal patch taught in Manoj K. Mishra, *Microcapsules and Transdermal Patch: A Comparative Approach for Improved Delivery of Antidiabetic Drug,* 10 AAPS PHARM. SCI. TECH. 3, 928-34 (2009), which is hereby incorporated by reference in its entirely. Optionally, the drug may be administered through a transdermal gel as taught in Srinivas Mutalik & Nayanabhirama Udupa, *Pharmacological Evaluation of Membrane-Moderated Transdermal Systems of Glipizide,* 33 CLINICAL & EXPERIMENTAL PHARMACOLOGY & PHYSIOLOGY, 17-26 (2006), which is hereby incorporated by reference in its entirety. For example, transdermal administration may be used for subjects with chronic conditions who may benefit from continuous and/or prolonged administration of SUR1-TRPM4 channel inhibitors. The transdermal administration may occur for any duration disclosed above. Administration through a transdermal patch or gel may occur prior to, simultaneously with, and/or after the onset of cerebral edema-related side effects or the initiation of the cerebral edema prone treatment, or any combination thereof. In further embodiments, the transdermal administration may accompany an oral, injection, or infusion administration disclosed above or combinations thereof.

In further embodiments, the SUR1-TRPM4 channel inhibitor is administered orally. The oral administration may be via capsules, tablets, pills, powders, liquid suspension, or other commonly used oral administration forms. The oral administration may occur prior to, during, or after the onset of cerebral edema-related side effects or the initiation of the cerebral edema prone treatment, or any combination thereof. In further embodiments, the oral administration may be combined with an injection, infusion, or transdermal administration route disclosed herein or combinations thereof.

In all embodiments, the administration of the SUR1-TRPM4 channel inhibitor can be intermittent, or at gradual, continuous, constant, or controlled rates. In addition, the time of day and the number of times per hour, day, week, or month that the compounds are administered can vary depending upon desired dosages.

Dosage Determinations

As used herein, the term "dose" and its grammatical derivatives and equivalents refers to the amount of SUR1-TRPM4 channel inhibitor administered to a subject. A dose may be described in terms of weight of a SUR1-TRPM4 channel inhibitor administered per day, in terms of the weight of SUR1-TRPM4 channel inhibitor per volume, or in equivalent types of measurements. The term "effective amount" or "effective dose" refers to the amount of a compound (e.g., a compound of the present invention) sufficient to effect beneficial or desired results. An effective amount can be administered in one or more administrations, applications or dosages and is not intended to be limited to a particular formulation or administration route.

It is understood that an effective amount of a SUR1-TRPM4 channel inhibitor as a treatment may vary depending on several factors including the specific subject receiving the administration, the administration route, the likelihood or severity of the cerebral edema, the duration or amount of cerebral edema prone treatment, and other procedure specific conditions. It will also be understood that dosages will vary between different SUR1-TRPM4 channel inhibitors.

In one embodiment of the invention, the effective dosage level is measured in mg of SUR1-TRPM4 channel inhibitor per day and ranges from about 0.05 mg/day to about 3.0 mg/day. For example, a suitable daily dose of SUR1-TRPM4 channel inhibitor may be less than about 3.0 mg per day. For example, a suitable daily dose of glyburide may be about 2.5-3.0 mg/day, or about 2.0-2.5 mg/day, or about 1.5-2.0 mg/day, or about 1.0-1.5 mg/day, or about 0.4-1.0 mg/day, or about 0.05-0.4 mg/day. Additionally, the suitable daily dose may be about 0.05 mg/day, or about 0.25 mg/day, or about 0.5 mg/day, or about 1.0 mg/day, or about 1.5 mg/day, or about 2.0 mg/day, or about 2.5 mg/day, or about 3.0 mg/day. The effective dose for a given patient may also range from about 0.05 mg/day to about 3.0 mg/day, or from about 0.5 mg/day to about 2.5 mg/day, or from about 1.0 mg/day to about 2.0 mg/day. The SUR1-TRPM4 dosage levels are calculated in mg/day for illustrative purposes but the listed ranges are intended to include analogous dosages calculated in any weight unit per hour, day, week, month, treatment session, or similar time period.

Optionally, the dose range of the SUR1-TRPM4 channel inhibitor is an amount that yields a SUR1-TRPM4 blood plasma level of about 0.4 ng/mL to about 5 ng/mL. Suitable blood plasma concentrations include about 5 ng/mL, or about 4.5 ng/mL, or about 4 ng/mL, or about 3.5 ng/mL, or about 3 ng/mL, or about 2.5 ng/mL, or about 2 ng/mL or about 1.5 ng/mL, or about 1 ng/mL, or about 0.5 ng/mL, or similar blood plasma concentrations. In some embodiments, the suitable blood plasma concentration of the SUR1-TRPM4 inhibitor may be about 0.4-1.0 ng/mL, or about 1.0-1.5 ng/mL, or about 1.5-2.0 ng/mL, or about 2.0-2.5 ng/mL, or about 2.5-3.0 ng/mL, or about 3.0-3.5 ng/mL, or about 3.5-4.0 ng/mL, or about 4.0-4.5 ng/mL, or about 4.5-5.0 ng/mL, or combinations thereof. A suitable plasma concentration may also fall in the range of about 0.5 ng/mL to about 5.0 ng/mL, or of about 1.0 ng/mL to about 4.5 ng/mL, or of about 1.5 ng/mL to about 4.0 ng/mL, or of about 2.0 ng/mL to about 3.5 ng/mL, or of about 2.5 ng/mL to about 3.0 ng/mL. The amounts listed are intended for illustrative purposes and it is understood that any dosage levels substantially similar to those listed are covered by the present invention. The ranges are also intended to encompass analogous ranges measured in any units of weight of drug per any unit of blood plasma volume.

Optionally, the effective dose level is one that reaches a maximum SUR1-TRPM4 channel inhibitor plasma concentration level (denoted as "$C_{max}$") of about 1 ng/mL to about 30 ng/mL. Suitable maximum SUR1-TRPM4 channel concentrations include about 30 ng/mL, about 28 ng/mL, about 26 ng/mL, about 24 ng/ML, about 22 ng/mL, about 20 ng/mL, about 18 ng/mL, about 16 ng/mL, about 14 ng/mL, about 12 ng/mL, about 10 ng/mL, about 8 ng/mL, about 6 ng/mL, about 4 ng/mL, about 2 ng/mL, or about 1 ng/mL, or similar concentration levels. A suitable maximum concentration level may also fall in the range of about 1-2 ng/mL, about 2-4 ng/mL, about 4-6 ng/mL, about 6-8 ng/mL, about 8-10 ng/mL, about 10-12 ng/mL, about 12-14 ng/mL, about 14-16 ng/mL, about 16-18 ng/mL, about 18-20 ng/mL, about 20-22 ng/mL, about 22-24 ng/mL, about 24-26 ng/mL, about 26-28 ng/mL, or about 28-30 ng/mL. It is understood that any dosage levels substantially similar to those listed are covered by the present invention. The ranges are intended to encompass analogous ranges measured in any units of weight of drug per any unit of volume.

Optionally, the effective dose level is one that achieves a steady-state SUR1-TRPM4 concentration of about 3.0 ng/mL to about 30.0 ng/mL. Thus, in embodiments, treatment will result in stead-state blood plasma concentrations of about 30 ng/mL, about 27 ng/mL, about 24 ng/mL, about 21 ng/mL, about 18 ng/mL, about 15 ng/mL, about 12 ng/mL, about 9 ng/mL, about 6 ng/mL, about 3 ng/mL, or anywhere between the listed concentrations. In other embodiments, the desired effective steady-state concentration may be about 3.0-5.0 ng/mL, or about 5.0-7.0 ng/mL, or about 7.0-10.0 ng/mL, or about 10.0-12.0 ng/mL, or about 12.0-14.0 ng/mL, or about 14.0-16.0 ng/mL, or about 16.0-18.0 ng/mL, or about 18.0-20.0 ng/mL, or about 20.0-22.0 ng/mL, 22.0-24.0 ng/mL, or about 24.0-26.0 ng/mL, or about 26.0-28.0 ng/mL, or about 28.0-30.0 ng/mL, or combinations thereof. In further embodiments, a steady-state concentration of about 3.0 ng/mL to about 30.0 ng/mL, or about 5.0 ng/mL to about 28.0 ng/mL, or about 7.0 ng/mL to about 26.0 ng/mL, or about 9.0 ng/mL to about 24.0 ng/mL, or about 11.0 ng/mL to about 22.0 ng/mL, or about 13.0 ng/mL to about 20.0 ng/mL, or about 15.0 ng/mL to about 18.0 ng/mL, or about 16.0 ng/mL to about 17.0 ng/mL, or combinations thereof may be desired. The desired steady-state concentration may vary depending on several factors, including the likelihood and/or severity of cerebral edema, and may change over time. The ranges disclosed are exemplary and are intended to encompass analogous ranges measured in any units of weight per volume.

The specific effective dose for any particular patient will depend on a variety of factors including the severity or likelihood of the condition; activity of the specific compound employed; the age, body weight, general health, sex and diet of the patient; the preparation of the specific compound; the time and route of administration; the duration of administration; therapeutic agents used in combination or coinciding with the specific compound employed; and like factors known in the medical arts. The effective dose may also change over time as any of the cerebral edema-related side effects worsen or improve. For chronic conditions, subjects may receive an effective dose for a plurality of days, weeks, or months. The number of and frequency of administrations may vary depending upon the likelihood or severity of the cerebral edema-related side effects and the patient specific response to the particular SUR1-TRPM4 channel inhibitor administered.

For any compound used in the methods described herein, the effective dose may be estimated initially from cell based assays. A dosage may be formulated in animal models to achieve a desired circulating plasma concentration range. Such information can be used to more accurately determine useful doses in humans.

Radiation Therapies Associated with Cerebral Edema

Radiation therapy is a useful treatment against cancerous cells throughout the body. Gamma radiation is delivered to cancerous tumors to stop the propagation of cancerous cells. Radiation therapy works by degrading the DNA in cells either directly or by the creation of free radicals. Radiation acts on cancerous as well as healthy cells. Healthy cells affected by radiation swell because the free radicals or direct radiation alter the permeability of their cell membranes, thereby allowing ions and excess fluid to enter the cell. See AM. BRAIN TUMOR ASS'N, *Conventional Radiation Therapy*, 1-14 (2016), hereby incorporated by reference in its entirety. The cellular swelling causes cerebral edema, and may worsen the symptoms of a brain tumor.

Administration of a SUR1-TRPM4 channel inhibitor can combat the cerebral edema caused by radiation therapy. The SUR1-TRPM4 channel inhibitor acts to regulate the ion channels in the cell membranes and thereby normalize the ion gradient and fluid flow between the intracellular and extracellular space. The normalized gradient and fluid flow are effective to reduce or prevent cellular swelling, which treats or prevents cerebral edema.

The radiation therapy may be administered by any method known in the medical arts. For example, sophisticated robotic systems such as the Cyberknife or Gamma Knife may be used to administer the radiation therapy. The administration of a SUR1-TRPM4 channel inhibitor may allow for Gamma Knife or Cyberknife procedures to occur that would previously would have been impossible or prohibitively dangerous due to fear of cerebral edema. Administration of SUR1-TRPM4 channel inhibitors to subjects receiving radiation therapy may reduce or eliminate the need for anti-inflammatory drugs and other therapeutic agents current administered to radiation patients, many of which have known adverse side effects. For example, administration of a SUR1-TRPM4 channel inhibitor may reduce the need for dexamethasone, which is known to cause several adverse side effects such as seizures, depression, hypoglycemia, pancreatitis, and others.

Radiation therapy directed at a brain tumor is most likely to cause cerebral edema, but, as used herein, radiation therapy may refer to therapeutic, prophylactic, or palliative radiation applied to the brain or in close proximity to the brain. It is also contemplated that prolonged radiation therapy for cancers in other locations, such as the lungs or mammary glands, can lead to cerebral edema due to the free radicals introduced to the body. Several cancers are likely to metastasize to the brain and administration of a SUR1-TRPM4 channel inhibitor prior to or following the metastasis can prevent or reduce cerebral edema caused by the metastasis. The primary or secondary tumor may repeatedly metastasize to the brain, increasing the cerebral edema. Cancers that may lead to cerebral edema include, but are not limited to, lung cancer, breast cancer, melanoma, Lymphoma, GI tract cancers, Genitourinary tract cancer, Osteosarcoma, head and neck cancers, combinations thereof, or any other systemic cancers likely to metastasize to the brain.

In some embodiments, the SUR1-TRPM4 channel inhibitor may be administered prior to and/or during and/or after the initiation of the radiation therapy. In further embodiments, the SUR1-TRPM4 channel inhibitor may be administered prior to and/or after the onset of the cerebral edema associated with the radiation therapy.

SUR1-TRPM4 Administration

The manner and duration of administering SUR1-TRPM4 channel inhibitor may vary. Regardless of administration route, embodiments may be administered for about 1 to about 96 hours or longer. For example, the administration duration may be from about 1-5 hours, from about 5-10 hours, from about 10-15 hours, from about 15-20 hours, from about 20-25 hours, from about 25-30 hours, from about 30-35 hours, from about 35-40 hours, from about 40-45 hours, from about 45-50 hours, from about 50-55 hours, from about 55-60 hours, from about 60-65 hours, from about 65-70 hours, from about 70-75 hours, from about 75-80 hours, from about 80-85 hours, from about 85-90 hours, or from about 90-96 hours. In other embodiments, administration of the SUR1-TRPM4 channel inhibitor extends over periods of more than about 5 hours, or more than about 10 hours, or more than about 20 hours, or more than about 30 hours, or more than about 40 hours, or more than about 50 hours, or more than about 60 hours, or more than about 70 hours, or more than about 80 hours, or more than about 90 hours. In further embodiments, the SUR1-TRPM4 inhibitor administration last from about 5 hours to about 90 hours, from about 15 hours to about 80 hours, from about 25 hours to about 70 hours, from about 35 hours to about 60 hours, or from about 45 to 50 hours.

In other embodiments, the administration may occur for an extended period of time, such as a period of about one day, or about two days, or about three days, or about four days, or about five days, or more. For patients with chronic conditions, the administration may last even longer, such as several days, or about 1 week, or about 2 weeks, or about 3 weeks, or more until symptoms subside.

In further embodiments, the SUR1-TRPM4 administration may occur about 6 hours or less prior to the initiation of the radiation therapy. As such, embodiments may begin administration about 6 hours prior to the initiation of the radiation therapy, about 5 hours prior to the initiation of the radiation therapy, about 4 hours prior to the initiation of the radiation therapy, about 3 hours prior to the initiation of the radiation therapy, about 2 hours prior to the initiation of the radiation therapy, or about 1 hour or less prior to the initiation of the radiation therapy. Such embodiments may administer the SUR1-TRPM4 channel inhibitor intermittently for a duration listed above or continuously for the duration listed above.

For any given administration duration, the administration may occur continuously or as a series of separate administrations, and also may include more than one SUR1-TRPM4 channel inhibitor and/or more than one route of administration.

In some embodiments, the SUR1-TRPM4 channel inhibitor is administered via one or more continuous infusions. A continuous infusion is an intravenous administration that may last for any of the above listed durations. In further embodiments, the administration includes at least two continuous infusions where there is about 1 to several minutes, about 1 to several hours, about 1 to several days, or about 1 to several months between the multiple continuous infusions. The at least two continuous infusions may administer the same or different SUR1-TRPM4 channel inhibitors.

In some embodiments, the SUR1-TRPM4 channel inhibitor administration is achieved by injection. An injection is an intravenous administration that may be continuous or bolus in form. A continuous injection is one that lasts for any duration stated above. A bolus injection refers to administration of the SUR1-TRPM4 channel inhibitor in a single injection that lasts for a relatively short period of time, usually a period of about 3 minutes or less. Several bolus injections may be administered in series for any of the durations disclosed above.

In further embodiments, the methods of administration include administration of the SUR1-TRPM4 channel inhibitor in a bolus injection to a subject, followed by a continuous infusion of the SUR1-TRPM4 channel inhibitor and by one or more further bolus injections of the SUR1-TRPM4 channel inhibitor. In embodiments, a second bolus injection is administered substantially immediately after the completion of the continuous infusion. For example, the second bolus administration commences less than one hour, or less than 30 minutes, or less than 10 minutes, or less than 5 minutes, or less than 3 minutes, or less than 2 minutes, or less than 1 minute, after the completion of the continuous infusion. A third bolus injection may begin after the completion of the second continuous infusion, and may begin either substantially immediately after the completion of the second continuous infusion, or may begin after an extended period of time after the completion of the second continuous infusion. Similarly, a fourth, or fifth, or other further bolus injection, and/or further continuous infusion may be administered, either substantially immediately, or after an extended period of time. It is contemplated that the entire sequence of bolus injections and continuous infusions may occur wholly prior to or after the onset of cerebral edema, or the sequence may be split between before, during, and after the onset of cerebral edema with one or more bolus injections and/or one or more continuous infusions occurring before, one or more bolus injections and/or continuous administrations occurring during, and/or one or more bolus injections and/or continuous infusions occurring after the onset of cerebral edema. Intravenous administration methods disclosed in U.S. Pat. No. 9,254,259 may be used, which is hereby incorporated by reference in its entirety.

In other embodiments, the SUR1-TRPM4 channel inhibitor is administered transdermally. An advantage of transdermal administration is that it may be less invasive as compared to administration by infusion or injection and may be more effective than oral pathways. For example, the SUR1-TRPM4 channel inhibitor may be administered using a transdermal patch taught in Manoj K. Mishra, *Microcapsules and Transdermal Patch: A Comparative Approach for Improved Delivery of Antidiabetic Drug*, 10 AAPS PHARM. SCI. TECH. 3, 928-34 (2009), which is hereby incorporated by reference in its entirely. Optionally, the drug may be administered through a transdermal gel as taught in Srinivas Mutalik & Nayanabhirama Udupa, *Pharmacological Evaluation of Membrane-Moderated Transdermal Systems of Glipizide*, 33 CLINICAL & EXPERIMENTAL PHARMACOLOGY & PHYSIOLOGY, 17-26 (2006), which is hereby incorporated by reference in its entirety. For example, transdermal administration may be used for subjects with chronic conditions who may benefit from continuous and/or prolonged administration of SUR1-TRPM4 channel inhibitors. The transdermal administration may occur for any duration disclosed above. Administration through a transdermal patch or gel may occur prior to, simultaneously with, and/or after the onset of cerebral edema or the initiation of the radiation therapy, or any combination thereof. In further embodiments, the transdermal administration may accompany an oral, injection, or infusion administration disclosed above or combinations thereof.

In further embodiments, the SUR1-TRPM4 channel inhibitor is administered orally. The oral administration may be via capsules, tablets, pills, powders, liquid suspension, or other commonly used oral administration forms. The oral administration may occur prior to, during, or after the onset of cerebral edema or the initiation of the radiation therapy, or any combination thereof. In further embodiments, the oral administration may be combined with an injection, infusion, or transdermal administration route disclosed herein or combinations thereof.

In further embodiments, the SUR1-TRPM4 channel inhibitor may be administered by any combination of the administration routes disclosed herein. In one such embodiment, the subject may receive a continuous infusion (intravenous) prior to and/or during the radiation administration, followed by an oral and/or transdermal administration after the radiation therapy. The oral and/or transdermal administration may occur at the radiation therapy facility and/or be sent home with the subject via a prescription. The continuous infusion may begin around 6 hours prior to the radiation therapy and may last for any duration disclosed herein and may occur during and/or after the radiation therapy as well as prior to the radiation therapy. In some embodiments, the continuous infusion begins 6 hours prior to the radiation therapy and last for up to 24 hours. It is contemplated that the continuous infusion may begin around 6 hours, around 5 hours, around 4 hours, around 3 hours, around 2 hours, or around 1 hour prior to the beginning of the radiation therapy. The subsequent oral and/or transdermal administration may last for any duration disclosed herein or until symptoms subside. The dosage levels of the continuous infusion and the oral and/or transdermal administration may be the same or the oral and/or transdermal dosage may be lower than the continuous infusion dosage level. In another such embodiment, the subject receives the SUR1-TRPM4 channel inhibitor via the bolus injection and continuous infusion administration disclosed above and then receives the oral and/or transdermal administration following the radiation therapy. The continuous infusion and/or the bolus injection/continuous infusion combination may occur wholly prior to the radiation therapy or may occur prior to the radiation therapy as well as during and/or following the radiation therapy and may last for any duration disclosed herein.

In all embodiments, the administration of the SUR1-TRPM4 channel inhibitor can be intermittent, or at gradual, continuous, constant, or controlled rates. In addition, the time of day and the number of times per hour, day, week, or month that the compounds are administered can vary depending upon desired dosages.

Dosage Determinations

As used herein, the term "dose" and its grammatical derivatives and equivalents refers to the amount of SUR1-TRPM4 channel inhibitor administered to a subject. A dose may be described in terms of weight of a SUR1-TRPM4 channel inhibitor administered per day, in terms of the weight of SUR1-TRPM4 channel inhibitor per volume, or in equivalent types of measurements. The term "effective amount" or "effective dose" refers to the amount of a compound (e.g., a compound of the present invention) sufficient to effect beneficial or desired results. An effective amount can be administered in one or more administrations, applications or dosages and is not intended to be limited to a particular formulation or administration route.

It is understood that an effective amount of a SUR1-TRPM4 channel inhibitor as a treatment may vary depending on several factors including the specific subject receiving the administration, the administration route, the likelihood or severity of the cerebral edema, the duration or amount of radiation therapy, and other procedure specific conditions. It will also be understood that dosages will vary between different SUR1-TRPM4 channel inhibitors.

In one embodiment of the invention, the effective dosage level is measured in mg of SUR1-TRPM4 channel inhibitor per day and ranges from about 0.05 mg/day to about 3.0 mg/day. For example, a suitable daily dose of SUR1-TRPM4 channel inhibitor may be less than about 3.0 mg per day. For example, a suitable daily dose of glyburide may be about 2.5-3.0 mg/day, or about 2.0-2.5 mg/day, or about 1.5-2.0 mg/day, or about 1.0-1.5 mg/day, or about 0.4-1.0 mg/day, or about 0.05-0.4 mg/day. Additionally, the suitable daily dose may be about 0.05 mg/day, or about 0.25 mg/day, or about 0.5 mg/day, or about 1.0 mg/day, or about 1.5 mg/day, or about 2.0 mg/day, or about 2.5 mg/day, or about 3.0 mg/day. The effective dose for a given patient may also range from about 0.05 mg/day to about 3.0 mg/day, or from about 0.5 mg/day to about 2.5 mg/day, or from about 1.0 mg/day to about 2.0 mg/day. The SUR1-TRPM4 dosage levels are calculated in mg/day for illustrative purposes but the listed ranges are intended to include analogous dosages calculated in any weight unit per hour, day, week, month, treatment session, or similar time period.

Optionally, the dose range of the SUR1-TRPM4 channel inhibitor is an amount that yields a SUR1-TRPM4 blood plasma level of about 0.4 ng/mL to about 5 ng/mL. Suitable blood plasma concentrations include about 5 ng/mL, or about 4.5 ng/mL, or about 4 ng/mL, or about 3.5 ng/mL, or about 3 ng/mL, or about 2.5 ng/mL, or about 2 ng/mL or about 1.5 ng/mL, or about 1 ng/mL, or about 0.5 ng/mL, or similar blood plasma concentrations. In some embodiments, the suitable blood plasma concentration of the SUR1-TRPM4 inhibitor may be about 0.4-1.0 ng/mL, or about 1.0-1.5 ng/mL, or about 1.5-2.0 ng/mL, or about 2.0-2.5 ng/mL, or about 2.5-3.0 ng/mL, or about 3.0-3.5 ng/mL, or about 3.5-4.0 ng/mL, or about 4.0-4.5 ng/mL, or about 4.5-5.0 ng/mL, or combinations thereof. A suitable plasma concentration may also fall in the range of about 0.5 ng/mL to about 5.0 ng/mL, or of about 1.0 ng/mL to about 4.5 ng/mL, or of about 1.5 ng/mL to about 4.0 ng/mL, or of about 2.0 ng/mL to about 3.5 ng/mL, or of about 2.5 ng/mL to about 3.0 ng/mL. The amounts listed are intended for illustrative purposes and it is understood that any dosage levels substantially similar to those listed are covered by the present invention. The ranges are also intended to encompass analogous ranges measured in any units of weight of drug per any unit of blood plasma volume.

Optionally, the effective dose level is one that reaches a maximum SUR1-TRPM4 channel inhibitor plasma concentration level (denoted as "$C_{max}$") of about 1 ng/mL to about 30 ng/mL. Suitable maximum SUR1-TRPM4 channel concentrations include about 30 ng/mL, about 28 ng/mL, about 26 ng/mL, about 24 ng/ML, about 22 ng/mL, about 20 ng/mL, about 18 ng/mL, about 16 ng/mL, about 14 ng/mL, about 12 ng/mL, about 10 ng/mL, about 8 ng/mL, about 6 ng/mL, about 4 ng/mL, about 2 ng/mL, or about 1 ng/mL, or similar concentration levels. A suitable maximum concentration level may also fall in the range of about 1-2 ng/mL, about 2-4 ng/mL, about 4-6 ng/mL, about 6-8 ng/mL, about 8-10 ng/mL, about 10-12 ng/mL, about 12-14 ng/mL, about 14-16 ng/mL, about 16-18 ng/mL, about 18-20 ng/mL, about 20-22 ng/mL, about 22-24 ng/mL, about 24-26 ng/mL, about 26-28 ng/mL, or about 28-30 ng/mL. It is understood that any dosage levels substantially similar to those listed are covered by the present invention. The ranges are intended to encompass analogous ranges measured in any units of weight of drug per any unit of volume.

Optionally, the effective dose level is one that achieves a steady-state SUR1-TRPM4 concentration of about 3.0 ng/mL to about 30.0 ng/mL. Thus, in embodiments, treatment will result in stead-state blood plasma concentrations of about 30 ng/mL, about 27 ng/mL, about 24 ng/mL, about 21 ng/mL, about 18 ng/mL, about 15 ng/mL, about 12 ng/mL, about 9 ng/mL, about 6 ng/mL, about 3 ng/mL, or anywhere between the listed concentrations. In other embodiments, the desired effective steady-state concentration may be about 3.0-5.0 ng/mL, or about 5.0-7.0 ng/mL, or about 7.0-10.0 ng/mL, or about 10.0-12.0 ng/mL, or about 12.0-14.0 ng/mL, or about 14.0-16.0 ng/mL, or about 16.0-18.0 ng/mL, or about 18.0-20.0 ng/mL, or about 20.0-22.0 ng/mL, 22.0-24.0 ng/mL, or about 24.0-26.0 ng/mL, or about 26.0-28.0 ng/mL, or about 28.0-30.0 ng/mL, or combinations thereof. In further embodiments, a steady-state concentration of about 3.0 ng/mL to about 30.0 ng/mL, or about 5.0 ng/mL to about 28.0 ng/mL, or about 7.0 ng/mL to about 26.0 ng/mL, or about 9.0 ng/mL to about 24.0 ng/mL, or about 11.0 ng/mL to about 22.0 ng/mL, or about 13.0 ng/mL to about 20.0 ng/mL, or about 15.0 ng/mL to about 18.0 ng/mL, or about 16.0 ng/mL to about 17.0 ng/mL, or combinations thereof may be desired. The desired steady-state concentration may vary depending on several factors, including the likelihood and/or severity of edema, and may change over time. The ranges disclosed are exemplary and intended to encompass analogous ranges measured in any units of weight per volume.

In embodiments where more than one administration route is used, the dosage levels may be the same for each administration route or each may utilize a different dosage level. In particular embodiments where the patient is sent home with an oral and/or transdermal prescription, the dosage may be lower than the dosage used prior to, during, or immediately following the radiation therapy. It is also contemplated that the prescribed dosage level will gradually decrease over time as the cerebral edema subsides and/or gradually increase leading up to radiation therapy sessions or if cerebral edema persists.

The specific effective dose for any particular patient will depend on a variety of factors including the severity or likelihood of the condition; activity of the specific compound employed; the age, body weight, general health, sex and diet of the patient; the preparation of the specific compound; the time and route of administration; the duration of administration; therapeutic agents used in combination or coinciding with the specific compound employed; and like factors known in the medical arts. The effective dose may also change over time as the cerebral edema worsen or the amount of radiation administered changes. For chronic conditions, subjects may receive an effective dose for a plurality of days, weeks, or months. The number of and frequency of administrations may vary depending upon the likelihood or severity of the cerebral edema and the patient specific response to the particular SUR1-TRPM4 channel inhibitor administered.

For any compound used in the methods described herein, the effective dose may be estimated initially from cell based assays. A dosage may be formulated in animal models to achieve a desired circulating plasma concentration range. Such information can be used to more accurately determine useful doses in humans.

Migraine Headaches

A migraine headache is an episodic, severe headache that may last for an extended period and is often accompanied by intense gastrointestinal disturbances such as nausea or vomiting and hypersensitivity to light and/or sound. Migraines are thought to be caused by abnormal activity in the dura matter, such as edema, that interfere with the trigeminal nerve, sending intense neural signals throughout the body. See Bogduk, *Anatomy and Physiology of Headache*, 49 BIOMED. & PHARAMCO. THERAPY, 435-445 (1995), hereby incorporated by reference in its entirety. Less severe headaches are also thought to be the result of swelling in the dura matter or other areas of the brain. The migraine may be a sporadic or familial hemiplegic migraine, menstrual migraine, or other acute or sub-chronic migraine.

Administration of SUR1-TRPM4 channel inhibitors can reduce swelling in the dura matter and other areas of the brain by blocking SUR1-TRPM4 channels associated with ion and fluid flow between the intracellular and extracellular space, thereby reducing swelling in those areas. Co-administration of a second therapeutically active with the SUR1-TRPM4 channel inhibitor may increase the efficacy of the migraine treatment or help abate side effects of migraines such as intense pain. Examples of secondary therapeutically active agents that may be co-administered with the SUR1-TRPM4 channel inhibitors includes a pain reliever, triptan, glucocorticoid, antidepressant, anti-seizure drug, botox, combinations thereof, or similar compounds.

The administration of SUR1-TRPM4 channel inhibitors or the co-administration of the SUR1-TRPM4 channel inhibitor and the second therapeutically active compound may occur prior to the onset of the migraine, or after the onset of the migraine. In embodiments, the administration or co-administration may last for about 1 to 96 hours and be continuous or intermittent during this period.

SUR1-TRPM4 Administration and Co-Administration

The manner and duration of administering SUR1-TRPM4 channel inhibitor may vary. Regardless of administration route, embodiments may be administered for about 1 to about 96 hours or longer. For example, the administration duration may be from about 1-5 hours, from about 5-10 hours, from about 10-15 hours, from about 15-20 hours, from about 20-25 hours, from about 25-30 hours, from about 30-35 hours, from about 35-40 hours, from about 40-45 hours, from about 45-50 hours, from about 50-55 hours, from about 55-60 hours, from about 60-65 hours, from about 65-70 hours, from about 70-75 hours, from about 75-80 hours, from about 80-85 hours, from about 85-90 hours, or from about 90-96 hours. In other embodiments, administration of the SUR1-TRPM4 channel inhibitor extends over periods of more than about 5 hours, or more than about 10 hours, or more than about 20 hours, or more than about 30 hours, or more than about 40 hours, or more than about 50 hours, or more than about 60 hours, or more than about 70 hours, or more than about 80 hours, or more than about 90 hours. In further embodiments, the SUR1-TRPM4 inhibitor administration last from about 5 hours to about 90 hours, from about 15 hours to about 80 hours, from about 25 hours to about 70 hours, from about 35 hours to about 60 hours, or from about 45 to 50 hours. Co-administrations of SUR1-TRPM4 and the second therapeutically active compound may likewise last for any duration between about 1 and 96 hours or longer.

In other embodiments, the administration or co-administration may occur for an extended period of time, such as a period of about one day, or about two days, or about three days, or about four days, or about five days, or more. For patients with chronic conditions, the administration or co-administration may last even longer, such as several days, or about 1 week, or about 2 weeks, or about 3 weeks, or more until symptoms subside.

In some embodiments, the administration of the SUR1-TRPM4 channel inhibitor and/or second therapeutically active agent may be timed to begin with known causes of migraines or pre-migraine symptoms. For example, for menstrual migraines, the administration may begin around the beginning of the follicular phase, the beginning of the ovulatory phase, sometime between these two phases, or any time coinciding with a drop in estrogen levels. The drop in estrogen associated with these phases typically occurs between around days 10 to 18 of the menstrual cycle. For example, the SUR1-TRPM4 channel inhibitor and/or second therapeutically active agent would be administered preferably by oral, nasal, transdermal, bolus injection, or combinations thereof, with treatment for up to two weeks per month starting on about day 10 to 18, or about day 12 to 16, or about day 13 to 15, of the menstrual cycle. Menstrual migraines are exemplary, and similar dosing cycles may be utilized for other sub-chronic migraines, with doses of about 0.5-1.5 mg per day.

In some embodiments, the administration of the SUR1-TRPM4 channel inhibitor and/or second therapeutically active agent may occur for a relatively short duration and be effective for treating acute migraines, such as hemiplegic (including sporadic or familial) migraines. In such embodiments, the administration may occur for any duration disclosed herein, but more preferably occurs for up to about 24 hours, 22 hours, 20 hours, 18 hours, 16 hours, 14 hours, 12 hours, 10 hours, 8 hours, 6 hours, 4 hours, 2 hours or 1 hour. Symptomatic relief may occur, for example, at about 6 to 8 hours after the start of treatment. The treatment of these acute migraines may occur by infusion, oral, transdermal, and/or nasal administration. Hemiplegic migraines are exemplary, and similar dosing regimes may be utilized for other acute migraines, with doses of about 2-3 mg per day.

For any given administration or co-admiration duration, the administration or co-administration may occur continuously or as a series of separate administrations, and also may include more than one SUR1-TRPM4 channel inhibitor and/or more than one route of administration.

In some embodiments, the SUR1-TRPM4 channel inhibitor and/or the second therapeutically active agent is administered via one or more continuous infusions. A continuous infusion is an intravenous administration that may last for any of the above listed durations. In further embodiments, the administration or co-administration includes at least two continuous infusions where there is about 1 to several minutes, about 1 to several hours, about 1 to several days, or about 1 to several months between the multiple continuous infusions. The at least two continuous infusions may administer the same or different SUR1-TRPM4 channel inhibitors. The at least two continuous infusions may administer the same or different second therapeutically active agents. The at least two continuous infusions may administer a SUR1-TRPM4 channel inhibitor and/or the second therapeutically active agent.

In some embodiments, the SUR1-TRPM4 channel inhibitor administration and/or the second therapeutically active agent administration is achieved by injection. An injection is an intravenous administration that may be continuous or bolus in form. A continuous injection is one that lasts for any duration stated above. A bolus injection refers to administration of the SUR1-TRPM4 channel inhibitor and/or second therapeutically active agent in a single injection that lasts for a relatively short period of time, usually a period of about 3 minutes or less. Several bolus injections may be administered in series for any of the durations disclosed above. In some embodiments, the several bolus injections may administer one of or both of the SUR1-TRPM4 channel inhibitor and the second therapeutically active agent. In some embodiments, the several bolus injections may alternate between injections of SUR1-TRPM4 and the second therapeutically active agent, and the alternating injections may be performed in any order.

In further embodiments, the methods of administration or co-administration include administration of a bolus injection to a subject, followed by a continuous infusion and by one or more further bolus injections. In embodiments, a second bolus injection is administered substantially immediately after the completion of the continuous infusion. For example, the second bolus injection commences less than one hour, or less than 30 minutes, or less than 10 minutes, or less than 5 minutes, or less than 3 minutes, or less than 2 minutes, or less than 1 minute, after the completion of the continuous infusion. A third bolus injection may begin after the completion of the second continuous infusion, and may begin either substantially immediately after the completion of the second continuous infusion, or may begin after an extended period of time after the completion of the second continuous infusion. Similarly, a fourth, or fifth, or other further bolus injection, and/or further continuous infusion may be administered, either substantially immediately, or after an extended period of time. It is contemplated that the entire sequence of bolus injections and continuous infusions may occur wholly prior to or after the onset of the migraine, or the sequence may be split between before, during, and after the onset of the migraine with one or more bolus injections and/or one or more continuous infusions occurring before, one or more bolus injections and/or continuous administrations occurring during, and/or one or more bolus injections and/or continuous infusions occurring after the onset of the migraine. Intravenous administration methods disclosed in U.S. Pat. No. 9,254,259 may be used, which is hereby incorporated by reference in its entirety. In the preceding embodiments, any of the bolus injections or continuous infusions may be either SUR1-TRPM4 channel inhibitors or the second therapeutically active agent without limit. In the preceding embodiments, any of the bolus injections or continuous infusions may be both the SUR1-TRPM4 channel inhibitor and the second therapeutically active agent without limit.

In other embodiments, the SUR1-TRPM4 channel inhibitor and/or the second therapeutically active agent is administered transdermally. An advantage of transdermal administration is that it may be less invasive as compared to administration by infusion or injection and may be more effective than oral pathways. For example, the SUR1-TRPM4 channel inhibitor and/or the second therapeutically active agent may be administered using a transdermal patch taught in Manoj K. Mishra, *Microcapsules and Transdermal Patch: A Comparative Approach for Improved Delivery of Antidiabetic Drug,* 10 AAPS PHARM. SCI. TECH. 3, 928-34 (2009), which is hereby incorporated by reference in its entirely. Optionally, the drugs may be administered through a transdermal gel as taught in Srinivas Mutalik & Nayanabhirama Udupa, *Pharmacological Evaluation of Membrane-Moderated Transdermal Systems of Glipizide,* 33 CLINICAL & EXPERIMENTAL PHARMACOLOGY & PHYSIOLOGY, 17-26 (2006), which is hereby incorporated by reference in its entirety. For example, transdermal administration may be used for subjects with chronic conditions who may benefit from continuous and/or prolonged administration of SUR1-TRPM4 channel inhibitors and/or the second therapeutically active agent. The transdermal administration may occur for any duration disclosed above. Administration through a transdermal patch or gel may occur prior to, simultaneously with, and/or after the onset of the migraine, or any combination thereof. In further embodiments, the transdermal administration may accompany an oral, nasal, injection, or infusion administration disclosed above or combinations thereof.

In further embodiments, the SUR1-TRPM4 channel inhibitor and/or the second therapeutically active agent is administered orally. The oral administration may be via capsules, tablets, pills, powders, liquid suspension, or other commonly used oral administration forms. Oral administration may occur prior to, during, or after the onset of the migraine, or any combination thereof. In further embodiments, the oral administration may be combined with an injection, infusion, nasal, or transdermal administration route disclosed herein or combinations thereof.

In further embodiments, the SUR1-TRPM4 channel inhibitor and/or the second therapeutically active agent is administered nasally. Nasal administration may be particularly effective for treating acute migraines, such as hemiplegic migraines, or for treating sub-chronic migraines, such as menstrual migraines. The nasal administration may occur prior to, during, or after the onset of the migraine, or any combination thereof. In further embodiments, the nasal administration may be combined with an injection, infusion, transdermal, oral, or other administration route disclosed herein, or combinations thereof.

In all embodiments, the administration of the SUR1-TRPM4 channel inhibitor and/or the second therapeutically active agent can be intermittent, or at gradual, continuous, constant, or controlled rates. In addition, the time of day and the number of times per hour, day, week, or month that the compounds are administered can vary depending upon desired dosages.

In some co-administration embodiments, the SUR1-TRPM4 channel inhibitor and second therapeutically active agent are administered at substantially the same time. In other co-administration embodiments, one of the SUR1-TRPM4 channel inhibitor or the second therapeutically active agent are wholly administered prior to the other of the SUR1-TRPM4 channel inhibitor and the second therapeutically active agent. The time period between the administration of the SUR1-TRPM4 channel inhibitor and the administration of the second therapeutically active agent and/or the time period between administration of the second therapeutically active agent and the administration of the SUR1-TRPM4 channel inhibitor may be any of the durations listed above or may be much shorter, such about 2 minutes, about 5 minutes, about 10 minutes, about 15 minutes, about 20 minutes, or the like. In some embodiments, the administration of either the SUR1-TRPM4 channel inhibitor or the second therapeutically active agent can be initiated first and the other can be initiated second, and the period before initiation of administration of the first and initiation of administration of the second may be any time period such that there exist a period wherein both the SUR1-TRPM4 channel inhibitor and the second therapeutically active agent are simultaneously administered. The duration of the simultaneous administration may be the entire length of one, both, or neither of the SUR1-TRPM4 channel inhibitor administration and the second therapeutically active agent administration.

In all co-administration embodiments, the SUR1-TRPM4 channel inhibitor may be administered by any of the administration routes disclosed herein and the second therapeutically active agent may also be administered by any administration route disclosed herein. In all co-administration embodiments, the SUR1-TRPM4 channel inhibitor may be administered for any administration duration disclosed herein and the second therapeutically active agent may also be administered for any administration duration disclosed herein. The administration of the SUR1-TRPM4 channel inhibitor and the second therapeutically active agent do not have to be through the same administration route or form, or for the same administration duration, though they may be.

Dosage Determinations

As used herein, the term "dose" and its grammatical derivatives and equivalents refers to the amount of SUR1-TRPM4 channel inhibitor administered to a subject. A dose may be described in terms of weight of a drug administered per day, in terms of the weight of a drug per volume, or in equivalent types of measurements. The term "effective amount" or "effective dose" refers to the amount of a compound (e.g., a compound of the present invention) sufficient to effect beneficial or desired results. An effective amount can be administered in one or more administrations, applications or dosages and is not intended to be limited to a particular formulation or administration route.

It is understood that an effective amount of a SUR1-TRPM4 channel inhibitor and/or second therapeutically active agent as a treatment may vary depending on several factors including the specific subject receiving the administration, the administration route, the likelihood or severity of the migraine, and other procedure specific conditions. It will also be understood that dosages will vary between different SUR1-TRPM4 channel inhibitors and/or second therapeutically active agents.

In one embodiment of the invention, the effective dosage level is measured in mg of SUR1-TRPM4 channel inhibitor per day and ranges from about 0.05 mg/day to about 3.0 mg/day. For example, a suitable daily dose of SUR1-TRPM4 channel inhibitor may be less than about 3.0 mg per day. For example, a suitable daily dose of glyburide may be about 2.5-3.0 mg/day, or about 2.0-2.5 mg/day, or about 1.5-2.0 mg/day, or about 1.0-1.5 mg/day, or about 0.4-1.0 mg/day, or about 0.05-0.4 mg/day. Additionally, the suitable daily dose may be about 0.05 mg/day, or about 0.25 mg/day, or about 0.5 mg/day, or about 1.0 mg/day, or about 1.5 mg/day, or about 2.0 mg/day, or about 2.5 mg/day, or about 3.0 mg/day. The effective dose for a given patient may also range from about 0.05 mg/day to about 3.0 mg/day, or from about 0.5 mg/day to about 2.5 mg/day, or from about 1.0 mg/day to about 2.0 mg/day. The SUR1-TRPM4 dosage levels are calculated in mg/day for illustrative purposes but the listed ranges are intended to include analogous dosages calculated in any weight unit per hour, day, week, month, treatment session, or similar time period. The suitable daily dose of the second therapeutically active agent are in the same ranges as that of SUR1-TRPM4 channel inhibitors. The daily dose of the SUR1-TRPM4 channel inhibitor and the second therapeutically active agent may be substantially the same, or may vary.

Optionally, the dose range of the SUR1-TRPM4 channel inhibitor is an amount that yields a SUR1-TRPM4 blood plasma level of about 0.4 ng/mL to about 5 ng/mL. Suitable blood plasma concentrations include about 5 ng/mL, or about 4.5 ng/mL, or about 4 ng/mL, or about 3.5 ng/mL, or about 3 ng/mL, or about 2.5 ng/mL, or about 2 ng/mL or about 1.5 ng/mL, or about 1 ng/mL, or about 0.5 ng/mL, or similar blood plasma concentrations. In some embodiments, the suitable blood plasma concentration of the SUR1-TRPM4 inhibitor may be about 0.4-1.0 ng/mL, or about 1.0-1.5 ng/mL, or about 1.5-2.0 ng/mL, or about 2.0-2.5 ng/mL, or about 2.5-3.0 ng/mL, or about 3.0-3.5 ng/mL, or about 3.5-4.0 ng/mL, or about 4.0-4.5 ng/mL, or about 4.5-5.0 ng/mL, or combinations thereof. A suitable plasma concentration may also fall in the range of about 0.5 ng/mL to about 5.0 ng/mL, or of about 1.0 ng/mL to about 4.5 ng/mL, or of about 1.5 ng/mL to about 4.0 ng/mL, or of about 2.0 ng/mL to about 3.5 ng/mL, or of about 2.5 ng/mL to about 3.0 ng/mL. The amounts listed are intended for illustrative purposes and it is understood that any dosage levels substantially similar to those listed are covered by the present invention. The ranges are also intended to encompass analogous ranges measured in any units of weight of drug per any unit of blood plasma volume. Suitable plasma concentrations of the second therapeutically active agent are in the same ranges as that of SUR1-TRPM4 channel inhibitors. The plasma concentration of the SUR1-TRPM4 channel inhibitor and the second therapeutically active agent may be substantially the same, or may vary.

Optionally, the effective dose level is one that reaches a maximum SUR1-TRPM4 channel inhibitor plasma concentration level (denoted as "$C_{max}$") of about 1 ng/mL to about 30 ng/mL. Suitable maximum SUR1-TRPM4 channel concentrations include about 30 ng/mL, about 28 ng/mL, about 26 ng/mL, about 24 ng/ML, about 22 ng/mL, about 20 ng/mL, about 18 ng/mL, about 16 ng/mL, about 14 ng/mL, about 12 ng/mL, about 10 ng/mL, about 8 ng/mL, about 6 ng/mL, about 4 ng/mL, about 2 ng/mL, or about 1 ng/mL, or similar concentration levels. A suitable maximum concentration level may also fall in the range of about 1-2 ng/mL, about 2-4 ng/mL, about 4-6 ng/mL, about 6-8 ng/mL, about 8-10 ng/mL, about 10-12 ng/mL, about 12-14 ng/mL, about 14-16 ng/mL, about 16-18 ng/mL, about 18-20 ng/mL, about 20-22 ng/mL, about 22-24 ng/mL, about 24-26 ng/mL, about 26-28 ng/mL, or about 28-30 ng/mL. It is understood that any dosage levels substantially similar to those listed are covered by the present invention. The ranges are intended to encompass analogous ranges measured in any units of weight of drug per any unit of volume. Suitable maximum concentrations of the second therapeutically active agent are in the same ranges as that of SUR1-TRPM4 channel inhibitors. The maximum concentration of the SUR1-TRPM4 channel inhibitor and the second therapeutically active agent may be substantially the same, or may vary Optionally, the effective dose level is one that achieves a steady-state SUR1-TRPM4 concentration of about 3.0 ng/mL to about 30.0 ng/mL. Thus, in embodiments, treatment will result in stead-state blood plasma concentrations of about 30 ng/mL, about 27 ng/mL, about 24 ng/mL, about 21 ng/mL, about 18 ng/mL, about 15 ng/mL, about 12 ng/mL, about 9 ng/mL, about 6 ng/mL, about 3 ng/mL, or anywhere between the listed concentrations. In other embodiments, the desired effective steady-state concentration may be about 3.0-5.0 ng/mL, or about 5.0-7.0 ng/mL, or about 7.0-10.0 ng/mL, or about 10.0-12.0 ng/mL, or about 12.0-14.0 ng/mL, or about 14.0-16.0 ng/mL, or about 16.0-18.0 ng/mL, or about 18.0-20.0 ng/mL, or about 20.0-22.0 ng/mL, 22.0-24.0 ng/mL, or about 24.0-26.0 ng/mL, or about 26.0-28.0 ng/mL, or about 28.0-30.0 ng/mL, or combinations thereof. In further embodiments, a steady-state concentration of about 3.0 ng/mL to about 30.0 ng/mL, or about 5.0 ng/mL to about 28.0 ng/mL, or about 7.0 ng/mL to about 26.0 ng/mL, or about 9.0 ng/mL to about 24.0 ng/mL, or about 11.0 ng/mL to about 22.0 ng/mL, or about 13.0 ng/mL to about 20.0 ng/mL, or about 15.0 ng/mL to about 18.0 ng/mL, or about 16.0 ng/mL to about 17.0 ng/mL, or combinations thereof may be desired. The desired steady-state concentration may vary depending on several factors, including the likelihood and/or severity of migraines, and may change over time. The ranges disclosed are exemplary and are intended to encompass analogous ranges measured in any units of weight per volume. The steady-state concentration of the second therapeutically active agent may be in the same ranges as that of SUR1-TRPM4 channel inhibitors. The steady state concentrations of the SUR1-TRPM4 channel inhibitor and the second therapeutically active agent may be substantially the same, or may vary.

The specific effective dose for any particular patient will depend on a variety of factors including the severity or likelihood of the migraine; activity of the specific compound employed; the age, body weight, general health, sex and diet of the patient; the preparation of the specific compound; the time and route of administration; the duration of administration; therapeutic agents used in combination or coinciding with the specific compound employed; and like factors known in the medical arts. The effective dose may also change over time as the migraines worsen or improve. For chronic conditions, subjects may receive an effective dose for a plurality of days, weeks, or months. The number of and frequency of administrations or co-administrations may vary depending upon the likelihood or severity of the migraines and the patient specific response to the particular SUR1-TRPM4 channel inhibitor administered and/or the second therapeutically active agent administered.

For any compound used in the methods described herein, the effective dose may be estimated initially from cell based assays. A dosage may be formulated in animal models to achieve a desired circulating plasma concentration range. Such information can be used to more accurately determine useful doses in humans.

EXAMPLES

Embodiments will be further described with reference to the following Examples, which are provided for illustrative purposes only and should not be used to limit the scope of or construe the invention.

Example 1

Proper Dosing Levels of Glyburide

To determine the proper dosage levels of SUR1-TRPM4, Glyburide was administered to 24 healthy adult subjects via a bolus injection followed by 72 hours of continuous infusion to determine the plasma concentration levels of glyburide throughout the study and the pharmacokinetic profile of the drug. Eight subjects received a bolus injection of 17.3 ng of glyburide followed by 0.4 mg/day of glyburide infusion for 72 hours. The remaining sixteen subjects received a bolus injection of 130 ng of glyburide followed by 3.0 mg/day of glyburide infusion for 72 hours. The two groups are referred to as the 0.4 mg/day group and the 3.0 mg/day group, respectively.

FIG. 1 shows the plasma glyburide concentration-time profiles in the subjects. The chart shows the glyburide concentrations in ng/mL on the vertical axis and the time on the horizontal axis. It is shown on a linear scale and includes the standard deviation for both the 0.4 mg/day group and the 3.0 mg/day group.

FIG. 2 shows the same plasma glyburide concentration time-profiles on a semi-logarithmic scale.

TABLE 1

| Pharmacokinetic Parameter | 17.3 µg bolus + 0.4 mg/day infusion for 72 hours (N = 8) | 130.0 µg bolus + 3.0 mg/day infusion for 72 hours (N = 16) |
| --- | --- | --- |
| Cmax$^a$ (ng/mL) | 2.983 (0.8948) | 23.26 (5.337) |
| AUC (hr · ng/mL) | 270 (101) | 1779 (536) |
| Css (ng/mL) | 3.702 (1.381) | 24.38 (7.350) |
| Css/D (ng/mL)/mg) | 3.025 (1.127) | 2.655 (0.8034) |
| V1, w (L/kg) | 0.0925 (0.0223) | 0.0843 (0.0138) |
| V2, w (L/kg) | 0.131 (0.0598) | 0.0922 (0.0201) |
| Vss, w (L/kg) | 0.224 (0.0669) | 0.176 (0.0245) |
| Vdarea, w (L/kg) | 0.341 (0.178) | 0.485 (0.274) |
| CL, w (L/hr/kg) | 0.0764 (0.0214) | 0.0837 (0.0258) |
| CLD2, w (L/hr/kg) | 0.0997 (0.0618) | 0.0276 (0.0164) |
| Alpha-HL (hr) | 0.346 (0.195) | 0.540 (0.229) |
| Beta-HL (hr) | 3.27 (1.66) | 4.05 (1.43) |

Source: Section 14, Table 14.7.2.
Abbreviations: N = number of subjects, D = dose, w = body weight, SD = standard deviation.
$^a$Values reported for Cmax are associated with bolus injection.

The mean steady-state glyburide concentration (Css) was 3.7 ng/mL for the 0.4 mg/day group, and 24.4 ng/mL for the 3.0 mg/day group. Steady-state was attained in accordance with the drug's terminal half-life, with no evidence of an accumulation of glyburide. Mean beta half-life (beta-HL), dose-corrected steady-state concentration (Css/D), and weight-corrected volume of the central compartment (V1, w), steady-state volume of distribution (Vss, w) and clearance (CL, w) values were similar between dose levels, consistent with dose-independent pharmacokinetics.

After the initial bolus RP-1127 IV injection, plasma M1 levels were first detected at 1 hour for the 0.4 mg/day dose group and at 10 minutes for the 3.0 mg/day dose group. Plasma M2 levels were first detectable at 2 hours for the 0.4 mg/day dose group and 20 minutes for the 3.0 mg/day dose group. Plasma M1 concentrations averaged ≤0.56 ng/mL in the 0.4 mg/day dose group and ≤4.4 ng/mL in the 3.0 mg/day dose group through 72.5 hours after the initial bolus injection. Plasma concentrations of M2 were considerably lower than those of M1, and averaged ≤0.19 ng/mL in the 0.4 mg/day dose group and ≤1.4 ng/mL in the 3.0 mg/day dose group through 72.5 hours after the initial bolus injection. Levels of the glyburide metabolites, M1 and M2, were considerably lower than those of glyburide, representing, on average, 18% and 6% of the glyburide steady-state concentration. Metabolite exposure was approximately proportional to the administered dose of RP-1127.

Example 2

Administration of Glyburide Following Administration of tPA

To show the efficacy of glyburide and similar compounds in preventing or treating adverse outcomes associated with tPA, a study involving 77 subjects with LHI was performed. The subjects were divided into four groups: Group 1 was administered tPA and a placebo; Group 2 was administered tPA and Cirara, a commercially available glyburide formulation; Group 3 was administered just a placebo with no tPA; Group 4 was administered Cirara with no tPA. As used herein, the term "placebo" refers to an ostensibly pharmaceutical formulation with no pharmaceutically active agent, or lacks the particular pharmaceutical agent of interest in a given study. In the examples disclosed herein, the placebo is lacking the SUR1-TRPM4 channel inhibitor. As used herein, the term "Cirara" refers to a commercially available intravenous formulation of glyburide. In this example, tPA was administered in accordance with current clinical guidelines for managing ischemic stroke within 4.5 hours of stroke onset (Jauch et al. 2013). It is used for exemplary reference to show the efficacy of glyburide and other SUR1-TRPM4 channel inhibitors in abating tPA associated adverse outcomes and is not intended to be limiting.

TABLE 2

Composition of the Experimental Groups and their Respective Administration

| Group Number | Number of Subjects | tPA | Administration Cirara | Placebo | Mortality Rate |
|---|---|---|---|---|---|
| 1 | 22 | Yes | — | Yes | 41% |
| 2 | 25 | Yes | Yes | — | 16% |
| 3 | 14 | — | — | Yes | 29% |
| 4 | 16 | — | Yes | — | 19% |

The adverse outcome examined in the study was death. This was for exemplary purposes only and is not intended to be limiting. At the end of the trial, Group 2, the one receiving both the glyburide containing drug and the tPA showed the lowest mortality rate at only 16%. In contrast, Group 1, receiving tPA and a placebo, showed the highest mortality rate at 41%. The baseline group, Group 3, received no tPA and no glyburide containing drug and showcase a mortality rate of 29%. Group 4 showed a mortality rate of 19%.

The fact that Group 1 had a higher mortality rate than the baseline group, Group 3, indicates that death is associated with the administration of tPA. The reduced mortality rate shown in Group 4 indicates that glyburide alone is effective for reducing death and other adverse outcomes, but the greatest showing of prevention of death ocurred when both glyburide and tPA were administered. This indicates that the administration of glyburide can reduce adverse outcomes associated with the administration of tPA.

FIG. 3 shows a bar graph comparing the outcome of the four groups described in this study. It is clear from the graph that the best outcome following the administration of tPA is achieved with a glyburide containing compound is administered.

Example 3

A clinical trial is performed to compare the effects of the SUR1-TRPM4 channel inhibitor glyburide administered to patients undergoing CAR-T therapy, surgical excision of a brain tumor, and/or diagnosed with cerebral edema to matched control patients.

This is a randomized, open-label, parallel group study investigating the effect of glyburide administered beginning on Day 1 after surgery, or on Day 1 after onset or diagnosis of cerebral edema-related side effects.

In one arm, glyburide is administered as a bolus followed by continuous infusion.

In a second arm, glyburide is administered via a transdermal patch or gel.

In a third arm, glyburide is administered via injection, e.g., intravenous infusion.

In a fourth arm, glyburide is administered orally.

Glyburide is administered at 0.5, 1, 1.5, 2, 2.5, or 3.0 mg/day.

The study duration is days up to weeks.

Plasma levels of glyburide are determined daily.

The control group is matched for age, gender, and preoperative stage. The control group does not receive treatment but receives adjuvant therapy post-surgery as per local standard practice.

Each patient is monitored via blood sampling and MRI. A diagnostic contrast-enhanced MRI of the brain is performed prior to inclusion in the study.

The following comparisons are made:
Occurrence of one or more cerebral edema-related side effects:
Headache
Neck pain or stiffness
Nausea or vomiting
Dizziness
Irregular breathing
Vision loss or changes
Memory loss
Inability to walk
Difficulty speaking
Stupor
Seizures
Loss of consciousness
Occurrence of Dose Limiting Toxicities (DLTs)

Occurrence of edema increase and initiation of dexamethasone (or any corticosteroid administration with the purpose of treating cerebral edema)
  ktrans change
  Fluid-attenuated inversion recovery (FLAIR) ratio change
  Incidence of Common Terminology Criteria for Adverse Events (CTCAE)
  Cerebral edema increase as measured on FLAIR volumetric imaging
  Occurrence of Post-operative Infections
  Post-operative Pain Control Results: Compared with the control group, the patient groups administered glyburide are found to have significantly reduced or inhibited cerebral edema-related side effects.

Example 4

A clinical trial is performed to compare the effects of the SUR1-TRPM4 channel inhibitor glyburide administered to patients diagnosed with brain tumors or metastasis and undergoing radiation therapy, e.g., gamma radiation, to matched control patients.

This is a randomized, open-label, parallel group study investigating the effect of glyburide administered beginning on Day 1 after radiation therapy.

In one arm, glyburide is administered as a bolus followed by continuous infusion.

In a second arm, glyburide is administered via a transdermal patch or gel.

In a third arm, glyburide is administered via injection, e.g., intravenous infusion.

In a fourth arm, glyburide is administered orally.

Glyburide is administered at 0.5, 1, 1.5, 2, 2.5, or 3.0 mg/day.

The study duration is weeks to months.

Plasma levels of glyburide are determined weekly.

The control group is matched for age, gender, and pre-radiation therapy stage. The control group does not receive glyburide treatment but receives placebo or corticosteroid, e.g., dexamethasone administration with the purpose of treating cerebral edema.

Each patient is monitored via blood sampling and MRI. A diagnostic contrast-enhanced MRI of the brain is performed prior to inclusion in the study.

The following comparisons are made:
Occurrence of one or more cerebral edema-related side effects:
  Headache
  Neck pain or stiffness
  Nausea or vomiting
  Dizziness
  Irregular breathing
  Vision loss or changes
  Memory loss
  Inability to walk
  Difficulty speaking
  Stupor
  Seizures
  Loss of consciousness
  Occurrence of Dose Limiting Toxicities (DLTs)
  Occurrence of edema increase and initiation of dexamethasone (or any corticosteroid administration with the purpose of treating cerebral edema)
  ktrans change
  Fluid-attenuated inversion recovery (FLAIR) ratio change
  Incidence of Common Terminology Criteria for Adverse Events (CTCAE)
  Cerebral edema increase as measured on FLAIR volumetric imaging
  Occurrence of Post-operative Infections
  Post-operative Pain Control Results: Compared with the control group, the patient groups administered glyburide are found to have significantly reduced or inhibited cerebral edema-related side effects.

Example 5

A clinical trial is performed to compare the effects of the SUR1-TRPM4 channel inhibitor glyburide administered to patients with a history of migraine.

This is a randomized, double-blind, placebo-controlled, parallel Group, dose-ranging study to investigate the efficacy, safety and tolerability of glyburide for the prevention of migraine.

In one arm, glyburide is administered as a bolus followed by continuous infusion.

In a second arm, glyburide is administered via a transdermal patch or gel.

In a third arm, glyburide is administered via injection, e.g., intravenous infusion.

In a fourth arm, glyburide is administered orally.

Glyburide is administered at 0.5, 1, 1.5, 2, 2.5, or 3.0 mg/day.

The study duration is several days up to one week.

Outcome Measures:
Number of migraine headache days during weeks 9-12 of the treatment period.

Change in Scores From Completeness of Response Survey (CORS) (Time Frame: Visit 1 (screening) and Visit 2 (study completion following 2-month treatment period)).

CORS scores for Pain (0-4), Associated Symptoms (0-4), Limbic/Affective Symptoms (0-5), and Speed of Return to Functionality (1-5), represent outcome measures that are relevant to patients. Higher scores represent better treatment efficacy.

The analysis compares CORS scores for usual treatment (pre-study) versus glyburide (study medication).
  Migraine frequency
  Migraine severity
  Migraine duration
  Occurrence of aura
  Functional impairment severity
  Rescue medication use
  Proportion of responders
  Global assessment of study medication Results: Compared with the placebo group, the patient groups administered glyburide have significantly improved migraine outcome measures after 12 weeks of treatment.

INCORPORATION BY REFERENCE

The entire disclosure of each of the patent documents and scientific articles referred to herein is incorporated by reference for all purposes.

EQUIVALENTS

The invention disclosed herein may be embodied in other specific forms without departing from the spirit or essential characteristics thereof. The foregoing embodiments are therefore to be considered in all respects illustrative rather than limiting of the invention. The scope of the invention is thus indicated by the appended claims rather than by the foregoing descriptions, and all changes that come within the meaning and range of equivalency of the claims are intended to be embraced therein.

What is claimed is:

1. A method of reducing mortality resulting from tissue plasminogen activator (tPA) administration in a subject that has been administered tPA, comprising administering an effective amount of a glyburide to the-subject.

2. The method of claim 1, where the subject has an Alberta Stroke Program Early CT Score (ASPECTS) that is equal to or less than 7.

3. The method of claim 1, wherein the glyburide is administered for about 1 hours to about 96 hours.

4. The method of claim 1, wherein at least a portion of the effective amount of the glyburide is administered prior to administration of tPA to the subject.

5. The method of claim 1, wherein at least a portion of the effective amount of the glyburide is administered simultaneously with administration of tPA to the subject.

6. The method of claim 1, wherein at least a portion of the effective amount of the glyburide is administered after administration of tPA to the subject.

7. The method of claim 1, wherein the glyburide is administered via one or more continuous infusions, via injection, via a transdermal patch or gel, orally, or a combination thereof.

8. The method of claim 1, wherein the glyburide is administered at a dosage of about 0.05 mg/day to about 3.0 mg/day.

9. The method of claim 1, comprising administering the glyburide in an amount sufficient to effect a glyburide plasma level of about 0.4 ng/mL to about 5 ng/mL in said subject.

10. The method of claim 1, comprising administering the glyburide in an amount sufficient to effect a steady state glyburide concentration of about 3.0 ng/mL to about 30.0 ng/mL in said subject.

11. The method of claim 1, comprising administering the glyburide in an amount sufficient to effect a $C_{max}$ of the glyburide of about 1 ng/mL to about 30 ng/mL in said subject.

* * * * *